(12) United States Patent
Brunner et al.

(10) Patent No.: US 11,980,657 B2
(45) Date of Patent: *May 14, 2024

(54) PEPTIDE VACCINES FOR HYPERCHOLESTEROLEMIA RELATED DISEASES

(71) Applicant: AFFIRIS CVD GMBH, Vienna (AT)

(72) Inventors: Sylvia Brunner, Vienna (AT); Gergana Galabova, Vienna (AT); Gabriele Winsauer, Vienna (AT); Erika Bilcikova, Bratislava (SK); Claudia Juno, Vienna (AT); Pola Linzmayer-Hirt, Wiener Neudorf (AT); Birgit Schuh, Vienna (AT); Guenther Staffler, Vienna (AT)

(73) Assignee: AFFIRIS CVD GMBH, Vienna (AT)

( * ) Notice: Subject to any disclaimer, the term of this patent is extended or adjusted under 35 U.S.C. 154(b) by 522 days.

This patent is subject to a terminal disclaimer.

(21) Appl. No.: 17/145,571

(22) Filed: Jan. 11, 2021

(65) Prior Publication Data

US 2021/0138048 A1 May 13, 2021

Related U.S. Application Data

(63) Continuation of application No. 15/984,800, filed on May 21, 2018, now Pat. No. 10,933,123, which is a continuation of application No. 15/367,711, filed on Dec. 2, 2016, now Pat. No. 9,999,659, which is a continuation of application No. 14/418,139, filed as application No. PCT/EP2013/067797 on Aug. 28, 2013, now Pat. No. 9,533,030.

(30) Foreign Application Priority Data

Aug. 29, 2012 (EP) .................................. 12182241

(51) Int. Cl.
| | | |
|---|---|---|
| A61K 39/00 | (2006.01) | |
| A61K 39/385 | (2006.01) | |
| A61K 39/39 | (2006.01) | |
| A61K 47/64 | (2017.01) | |
| C12N 9/64 | (2006.01) | |

(52) U.S. Cl.
CPC ........ *A61K 39/0005* (2013.01); *A61K 39/385* (2013.01); *A61K 39/39* (2013.01); *A61K 47/6415* (2017.08); *A61K 47/643* (2017.08); *A61K 47/646* (2017.08); *C12N 9/6424* (2013.01); *C12N 9/6454* (2013.01); *C12Y 304/21061* (2013.01); *A61K 2039/55505* (2013.01); *A61K 2039/6081* (2013.01)

(58) Field of Classification Search
CPC .. A61K 39/0005; A61K 39/39; C12N 9/6424; C12Y 304/21061; A61P 3/06
See application file for complete search history.

(56) References Cited

U.S. PATENT DOCUMENTS

2011/0052621 A1    3/2011    Champion et al.

FOREIGN PATENT DOCUMENTS

| JP | 2002-504886 A | 2/2002 |
| JP | 2005-504733 A | 2/2005 |
| WO | WO 2004/026897 | 4/2004 |
| WO | 2011/027257 A2 | 3/2011 |
| WO | WO 2011/027257 A2 | 3/2011 |
| WO | 2012/059573 A1 | 5/2012 |
| WO | 2013/037889 A2 | 3/2013 |

OTHER PUBLICATIONS

Lindblad E.B.—Aluminium adjuvants-in retrospect and prospect. Vaccine, 22, 3658-3668, 2004. (Year: 2004).*
Office Action as received in the corresponding CN Patent Application No. 201711057619.6 dated Oct. 10, 2020, (AW) 10, pages.
Paoia Lo Surdo, et al., "Mechanistic implications for LDL receptor degradation from the PCSK9/LDLR structure at neutral pH", EMBO reports, vol. 12, No. 12, (2011).
Jacques Genest, "Novel (Potential) Therapeutic Approaches," www.acclakelouise.com/downloads/slides/2012/1_Sunday_03_Genest_New._Lipids_Rx_pdf, XP002696435, Apr. 10, 2012, pp. 1-50.
Hai Li, et al., "Recent Patents on PCSK9: A New Target for Treating Hypercholesterolemia," Recent Patents on DNA & Gene Sequences 2009, vol. 3, No. 3, XP002619049, Nov. 1, 2009, pp. 201-212.
Anthony S. Wierzbicki, et al., "Inhibition of pre-protein convertase serine kexin-9 (PCSK-9) as a treatment for hyperlipidaemia," Expert Opinion on Investigational Drugs, Informa Healthcare, vol. 21, No. 5, XP009169248, May 1, 2012, pp. 667-676.
Daniel Steinberg, "An interpretive history of the cholesterol controversy, Part II. The early evidence linking hypercholesterolemia to coronary disease in humans," Journal of Lipid Research, vol. 46, 2005, errata and pp. 179-190.
Daniel Steinberg, "An interpretive history of the cholesterol controversy, part V: The discovery of the statins and the end of the controversy," Journal of Lipid Research, vol. 47, 2006, pp. 1339-1351.
Cynthia L. Brazolot Millan, et al., "CpG DNA can induce strong Th1 humoral and cell-mediated immune responses against hepatitis B surface antigen in young mice," Proc. Natl. Acad. Sci. USA, vol. 95, Dec. 1998, pp. 15553-15558.
Heather L. Davis, et al., "CpG DNA Is a Potent Enhancer of Specific Immunity in Mice Immunized with Recombinant Hepatitis B Surface Antigen," The Journal of Immunoiogy, http://www.JImmunol.org/content/160.2.870, 1998; 160: cover and pp. 870-876.
Pedro Garcia, et al., "Nucleotide sequence and expression of the pneumococcal autolysin gene from its own promoter in *Escherichia coli*," Gene 1618, 1986, pp. 265-272.

(Continued)

*Primary Examiner* — Elly-Gerald Stoica

(74) *Attorney, Agent, or Firm* — Oblon, McClelland, Maier & Neustadt, L.L.P.

(57) ABSTRACT

The present invention relates to a vaccine capable to induce the formation of antibodies directed to PCSK9 in vivo.

7 Claims, 9 Drawing Sheets

Figure 1A:
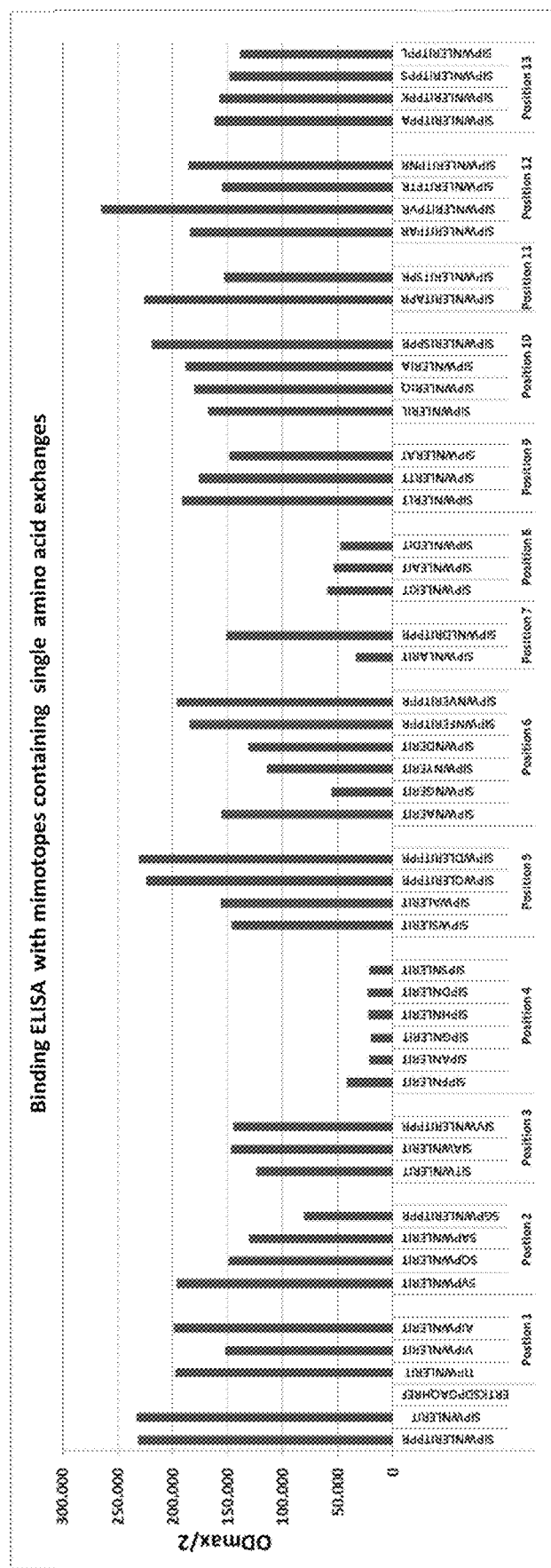

Specification includes a Sequence Listing.

(56) References Cited

OTHER PUBLICATIONS

Michael J. McCluskie, et al., "Cutting Edge: CpG DNA Is a Potent Enhancer of Systemic and Mucosal Immune Responses Against Hepatitis B Surface Antigen with Intranasal Administration to Mice," The Journal of Immunology, http://www.JImmunol/org/content/161/9/4463, J Immunol 1998; 161: cover and pp. 4463-4466.

Derek T. O'Hagan, et al., "Recent Advances in the Discovery and Delivery of Vaccine Adjuvants," Nature Reviews, Drug Discovery, vol. 2, Sep. 2003, pp. 727-735.

Yukio Sato, et al., "Immunostimulatory DNA Sequences Necessary for Effective Intradermal Gene Immunization," Science, vol. 273, Jul. 19, 1996, pp. 352-354.

Manmohan Singh, et al., "Advances in vaccine adjuvants," Nature Biotechnology, vol. 17, Nov. 1999, pp. 1075-1081.

International Search Report and Written Opinion of the International Searching Authority dated Feb. 17, 2014 in PCT/EP2013/067797 filed Aug. 28, 2013.

European Search Report dated May 2, 2013 in 12162241.5 filed Aug. 29, 2012.

\* cited by examiner

PEPTIDE VACCINES FOR HYPERCHOLESTEROLEMIA RELATED DISEASES

This is a continuation application of application Ser. No. 15/984,800, allowed, which is a divisional application of application Ser. No. 15/367,711 filed Dec. 2, 2016, now U.S. Pat. No. 9,999,659, which is a continuation of application Ser. No. 14/418,139, filed Jan. 29, 2015, now U.S. Pat. No. 9,533,030, which is the National Stage of International application No. PCT/EP2013/067797, filed Aug. 28, 2013, which claimed priority to European patent application no. 12182241.5, filed Aug. 29, 2012, of which all of the disclosures are incorporated herein by reference in their entireties.

The present invention relates to a vaccine capable to induce the formation of antibodies directed to PCSK9 in vivo.

The present invention relates to novel peptides which are able to influence the Proprotein Convertase Subtilisin/Kexin Type 9 (PCSK9)-mediated degradation of the Low Density Lipoprotein (LDL) receptor (LDLR). The peptides are coupled to an immunogenic carrier and formulated to a vaccine for the prevention and/or treatment of PCSK9-related health disorders caused by hyperlipidemia, hypercholesterolemia, or atherosclerosis.

One of the major leading causes of death worldwide is cardiovascular disease (CVD). Factors such as hyperlipidemia, hypercholesterolemia, hypertension and atherosclerosis are linked to those diseases. In comprehensive epidemiologic studies, a positive correlation between the level of the serum cholesterol and the occurrence of CVD could be demonstrated. High LDL cholesterol (LDLc) levels constitute a high cardiovascular risk, and are directly correlating with increased risk for atherosclerosis.

The LDLR, mainly hepatic LDLR, is the primary pathway for removal of LDLc from plasma. Circulating LDLc binds to the LDLR and the formed complex is internalized by clathrin-mediated endocytosis. Subsequently, while LDLc is proceeded for degradation, the LDLR is recycled back to the cell surface.

PCSK9 is a secreted serine protease that binds to and promotes degradation of the LDLR. It was discovered in 2003 as the third gene locus associated with autosomal dominant hypercholesterolemia (ADH). "Gain of function mutations" (GOF) of PCSK9 enhance its interaction with the LDLR and result in a decrease of LDLR levels and markedly higher LDLc levels. Consequently, GOF are associated with hypercholesterolemia and predisposition to atherosclerosis. Conversely, "Loss of function mutations" (LOF) lead to increased LDLR levels and dramatically reduced LDLc with a subsequent reduction of the risk for coronary heart disease (CHD). Human PCSK9 is mainly expressed in liver, intestine, and kidney. It is synthesized as a ~72 kDa protein which undergoes autocatalytic cleavage before it is secreted as a ~65 kDa mature protein.

Circulating PCSK9 binds specifically to the EGF-A domain of LDLR. The complex is internalized by endocytosis, and instead of recycling of the LDLR back to the cell surface, LDLR is consequently degraded in the lysosomes. The net effect of the PCSK9-LDLR interaction is the reduction of LDLR available for clearance of LDLc from plasma, indicating the importance of PCSK9 as a regulator of LDLR and thus LDLc metabolism.

Several animal studies substantiate the essential role of PCSK9 as a regulator of LDLc levels. Adenoviral overexpression of PCSK9 in mice led to a significant increase of circulating LDLc. In contrast, PCSK9−/− mice show a 2.8 fold increase in the levels of LDLR and a reduction of LDLc to ~50%, compared to wild type animals. GOF and LOF mutations indicate the important role of PCSK9 in regulating LDL metabolism in humans, making PCSK9 an attractive target for pharmaceutical intervention. Notably, humans heterozygous for LOF mutations in PCSK9 seem to be healthy and have a normal life-span. Moreover, a compound heterozygote with two inactivating mutations in PCSK9 and no circulating PCSK9 has been reported to be a healthy 31-year-old African-American mother with very low levels of LDLc (14-34 mg/dl).

Several compounds reducing the amount of circulating PCSK9 or inhibiting its interaction with the LDLR were successfully tested pre-clinically and clinically (such as monoclonal antibodies, antisense-oligonucleotides or inhibitors of autocatalysis). Although PCSK9 acts intracellularly and extracellularly on LDLR, targeting circulating PCSK9 is a valuable approach for LDLc lowering therapeutics. Parabiosis experiments in mice as well as administration of recombinant protein have indicated that extracellular PCSK9 is sufficient to reduce the number of hepatic LDLR. More importantly, results from human clinical studies with PCSK9-specific monoclonal antibodies (mAbs) indicate that targeting PCSK9 enables efficient and safe reduction of LDLc. In addition, several clinical trials to evaluate the safety and efficacy of targeting PCSK9 were recently successfully finalized.

WO 2012/059573 A1 and WO 2011/027257 A2 disclose fragments of the PCSK9 polypeptide as vaccines. Li et al. (Rec. Pat. DNA & Gene Seq. 3 (2009), 201-212) and Wierzbicki et al. (Exp. Op. Invest. Drugs 21 (2012), 667-676) report about recent developments regarding inhibition of PCSK9 for the treatment of hyperlipidaemia.

In summary, PCSK9 is a major regulator of LDLR, and thus LDLc levels. Although statins represent the first line of intervention for cholesterol management, statics are not sufficient or appropriate in certain subjects to achieve the goals. Moreover, PCSK9 was found to be upregulated by statins, counteracting their pharmacologic effect. Accordingly, the identification of additional or alternative medications to control LDLc levels is of great importance. Inhibition of PCSK9 is expected to lower plasma LDLc as monotherapy, but also to augment the cholesterol lowering effect of statics or other substances (such as for example fibrates or nicotinic acid).

An object of the present invention is to provide means and methods for reducing LDLc in an individual. This object can be achieved by providing peptides which mimic the respective native sequence, so-called mimotopes. Such mimotopes are able to induce antibodies that specifically bind to human PCSK9 and inhibit the PCSK9-mediated degradation of LDLR.

Therefore the present invention relates to a vaccine, vaccine composition or composition comprising at least one peptide consisting of 9 to 25 amino acid residues having the amino acid sequence (SEQ ID No. 1)
$$X_1X_2X_3WX_4X_5X_6RX_7(X_8)_m(X_9)_n,$$

wherein
$X_1$ is an amino acid residue selected from the group of uncharged amino acid residues, preferably selected from the group consisting of serine, threonine, valine and alanine, X$_2$ is an amino acid residue selected from the group of uncharged amino acid residues, preferably selected from the group of isoleucine, valine, glycine, glutamine and alanine, more preferably isoleucine, valine, glutamine and alanine.

X$_3$ is an amino acid residue selected from the group of uncharged amino acid residues, preferably selected from the group consisting of praline, threonine, alanine and valine, more preferably praline, X$_4$ is an amino acid residue selected from the group consisting of asparagine, serine, alanine, glutamine and aspartic acid, X$_5$ is an amino acid residue selected from the group consisting of leucine, glycine, alanine, tyrosine, aspartic acid, phenylalanine and valine, preferably leucine, X$_6$ is an amino acid residue selected from the group of hydrophilic, negatively charged amino acid residue, preferably an amino acid residue selected from the group consisting of glutamic acid and aspartic acid, X$_7$ is an amino acid residue selected from the group of uncharged amino acid residues, preferably selected from the group consisting of isoleucine, leucine, alanine and threonine, X$_8$ is an amino acid residue selected from the group of uncharged amino acid residues selected from the group consisting of threonine, leucine, glutamine, alanine and serine, X$_9$ is X$_{10}$X$_{11}$X$_{12}$ or a C-terminal truncated fragment thereof consisting of 1 or 2 amino acid residues, X$_{10}$ is any amino acid residue, preferably an amino acid residue selected from the group of uncharged amino acid residues, preferably selected from the group consisting of praline, alanine and serine, X$_{11}$ is any amino acid residue, preferably an amino acid residue selected from the group of uncharged amino acid residues, preferably selected from the group consisting of proline, alanine, valine, threonine and asparagine, X$_{12}$ is any amino acid residue, preferably an amino acid residue selected from the group consisting of arginine, alanine, lysine, serine, and leucine, m is 0 or 1, n is 0 or 1, and SEQ ID No. 1 is not SIPWNLERITPPR or a C-terminal truncated fragment thereof, wherein said at least one peptide is coupled or fused to a pharmaceutically acceptable carrier.

The vaccination of individuals with the peptides of the present invention leads to the production of polyclonal antibodies which bind to PCSK9. Such antibodies are able to compete with the LDLR binding. As a consequence, hepatic LDLR levels are increased and plasma LDLc and total cholesterol is decreased. Therefore, the administration of a vaccine according to the present invention allows treating or preventing diseases caused by hyperlipidemia, hypercholesterolemia and/or atherosclerosis.

The peptides of the present invention are so-called mimotopes. Mimotopes have an amino acid sequence which is different from the original protein/peptide sequence from which they are derived. Those mimotopes are considered as foreign by the immune system and therefore do not need to break self-tolerance.

The peptides of the present invention are variants (amino acid exchanges and optional truncations) of the PCSK9 fragment having amino acid sequence SIPWNLERITPPR (SEQ ID No. 2) and consist of 9 to 25 amino acid residues, preferably of 9 to 24, 9 to 23, 9 to 22, 9 to 21, 9 to 20, 9 to 19, 9 to 18, 9 to 17, 9 to 16, 9 to 15, 9 to 14, 9 to 13, 9 to 12, 9 to 11, 9 to 10 or 9 amino acid residues, more preferably of 9, 10, 11, 12, 13, 14, 15, 16, 17, 18, 19, 20, 21, 22, 23, 24 or 25 amino acid residues. It turned surprisingly out that a modification (e.g. mutation) of the tryptophan residue at position 4 of SEQ ID No. 2 and the arginine residue at position 8 of SEQ ID No. 2 results in the formation of antibodies which cannot bind sufficiently to PCKS9. The novel peptide sequences according to the present invention (especially if coupled to an immunogenic carrier and/or formulated as vaccines) are able to induce the formation of antibodies directed to PCSK9 and therefore beneficially modifying the PCSK9-mediated LDLR degradation and thus subsequently reduce plasma LDLc levels. The peptides defined with the present invention also achieve surprisingly superior results in reducing the levels of total cholesterol compared to the native PCSK9 sequences, even compared to the ones disclosed in WO 2012/059573 A1 and WO 2011/027257 A2. This is further shown in the example section of the present application by using a representative animal model. It is therefore specifically preferred to provide the peptide according to SEQ ID No. 1 with a length of 9 to 13 amino acid residues (i.e. wherein no X$_{12}$ is present and wherein m=1; or wherein m=0 and X$_{10}$ is proline, alanine and serine, and X$_{11}$ is proline, alanine, valine, threonine and asparagine and X$_{12}$ is arginine, alanine, lysine, serine and leucine).

Since the present invention is drawn to specific variants of the PCSK9 fragment having amino acid sequence SIPWNLERITPPR (SEQ ID No. 2), this original sequence and all its C-terminally truncated fragments are excluded by definition according to SEQ. ID No. 1 of the present invention. This makes clear that the original sequence SIPWNLERITPPR or C-terminally fragmented versions thereof, such as the peptides with the amino acid sequences SIPWNLERITPP, SIPWNLERITP, SIPWNLERIT, or SIPWNLERI (all derived from SEQ ID No. 2 by C-terminal deletion of amino acid(s)), are excluded from the definition of the peptide according to SEQ. ID No. 1 of the present invention in all their forms. Accordingly, it is also clear that these C-terminally truncated peptides are excluded as native peptides, as peptides coupled to a substrate with or without a linker, as peptides with a linker, such as a chemical linker or a Cys-linker, etc., especially, of course, if such peptides are provided as a vaccine.

The vaccine of the present invention may comprise at least one, at least 2, at least 3, at least 4, at least 5 or at least 10 peptides having amino acid sequence SEQ ID No. 1 as defined herein. Thus the vaccine may comprise a combination of two or more peptides as disclosed herein. However, it is also possible that the vaccine of the present invention comprises next to one or more peptides according to SEQ ID No. 1 and as defined herein also other peptides such as mimotopes (i.e. mutants of PCSK9 fragments) or fragments of PCSK9 (see e.g. WO 2011/027257). Particularly preferred fragments of PCSK9 are fragments of SIPWNLERITPPRYRADEYQPPDGGSLVEV, in particular SIPWNLERIT, SIPWNLERI, SIPWNLERITPPR, SIPWNLERITPP or SIPWNLERITP.

The peptides of the present invention can be chemically synthesized by methods which are well known in the art. Of course it is also possible to produce the peptides of the present invention using recombinant methods. The peptides can be produced in microorganisms such as bacteria, yeast or fungi, in eukaryotic cells such as mammalian or insect cells, or in a recombinant virus vector such as adenovirus, poxvirus, herpes virus, Simliki forest virus, baculovirus, bacteriophage, sindbis virus or Sendai virus. Suitable bacteria for producing the peptides include *E. coli, B. subtilis* or any other bacterium that is capable of expressing such peptides. Suitable yeast cells for expressing the peptides of the present invention include *Saccharomyces cerevisiae, Schizosaccharomyces pombe, Candida, Pichia pastoris* or any other yeast capable of expressing peptides. Corresponding means and methods are well known in the art. Also methods for isolating and purifying recombinantly produced peptides are well known in the art and include e.g. gel filtration, affinity chromatography, ion exchange chromatography etc.

To facilitate isolation of the peptides of the present invention, fusion polypeptides may be made wherein the peptides are translationally fused (covalently linked) to a heterologous polypeptide which enables isolation by affinity chromatography. Typical heterologous polypeptides are His-Tag (e.g. His6; 6 histidine residues), GST-Tag (Glutathione-S-transferase) etc. The fusion polypeptide facilitates not only the purification of the peptides but can also prevent the degradation of the peptides during the purification steps. If it is desired to remove the heterologous polypeptide after purification the fusion polypeptide may comprise a cleavage site at the junction between the peptide and the heterologous polypeptide. The cleavage site may consist of an amino acid sequence that is cleaved with an enzyme specific for the amino acid sequence at the site (e.g. proteases).

The vaccine and peptides of the present invention can be administered to any kind of mammal including humans. It is however preferred to administer the vaccine and peptides of the present invention to humans.

According to a preferred embodiment of the present invention $X_1$ is valine, serine, threonine or alanine, preferably valine.

According to a further preferred embodiment of the present invention $X_2$ is valine, alanine, isoleucine or glutamine, preferably valine.

According to a preferred embodiment of the present invention $X_3$ is proline, threonine, alanine or valine.

$X_4$ of SEQ ID No. 1 is preferably serine or asparagine, preferably serine.

According to a preferred embodiment of the present invention $X_6$ is glutamic acid.

$X_7$ is preferably leucine, isoleucine or threonine, preferably threonine.

$X_8$ is preferably glutamine, threonine or leucine.

According to a preferred embodiment of the present invention $X_1X_2X_3$ is selected from the group consisting of TIP, VIP, AIP, SVP, SQP, SAP, SGP, SIT, SIA, SIV and VQP.

According to a further preferred embodiment of the present invention $X_4X^5X_6$ is selected from the group consisting of SLE, ALE, QLE, DLE, NAE, NGE, NYE, NDE, NFE, NVE and NLD.

$X_7(X_8)_m$, m being 1, is preferably selected from the group consisting of LT, TT, AT, IL, IQ, IA, IS, TL, LQ and LL.

According to a preferred embodiment of the present invention $X_9$ is selected from the group consisting of PPR, PP, P, APR, SPR, PAR, PVR, PTR, PNR, PPA, PPK, PPS and PPL.

According to a particularly preferred embodiment of the present invention the at least one peptide is selected from the group consisting of TIPWNLERIT, TIPWNLERITPPR, VIPWNLERIT, VIPWNLERITPPR, AIPWNLERIT, AIPWNLERITPPR, SVPWNLERIT, SVPWNLERITPPR, SQPWNLERIT, SQPWNLERITPPR, SAPWNLERIT, SAPWNLERITPPR, SGPWNLERITPPR, SGPWNLERIT, SITWNLERIT, SITWNLERITPPR, SIAWNLERIT, SIAWNLERITPPR, SIVWNLERITPPR, SIVWNLERIT, SIPWALERIT, SIPWSLERITPPR, SIPWALERIT, SIPWALERITPPR, SIPWQLERITPPR, SIPWQLERIT, SIPWDLERITPPR, SIPWDLERIT, SIPWNAERIT, SIPWNAERITPPR, SIPWNGERIT, SIPWNGERLTPPR, SIPWNYERIT, SIPWNLERITPPR, SIPWNDERIT, SIPWNDERITPPR, SIPWNFERITPPR, SIPWNVERITPPR, SIPWNLDRITPPR, SIPWNFERIT, SIPWNVERIT, SIPWNLDRIT, SIPWNLERLT, SIPWNLERLTPPR, SIPWNLERTT, SIPWNLERTTPPR, SIPWNLERAT, SIPWNLERATPPR, SIPWNLERIL, SIPWNLERILPPR, SIPWNLERIQ, SIPWNLERIQPPR, SIPWNLERIA, SIPWNLERIAPPR, SIPWNLERISPPR, SIPWNLERIS, SIPWNLERITAPR, SIPWNLERITSPR, SIPWNLERITPAR, SIPWNLERITPVR, SIPWNLERITPTR, SIPWNLERITPNR, SIPWNLERITPPA, SIPWNLERITPPK, SIPWNLERITPPS, SIPWNLERITPPL, VIPWNLERLT, VIPWNLERLTPPR, VIPWNLERTT, VIPWNLERTTPPR, VIPWNLERIL, VIPWNLERILPPR, VIPWNLERIQ, VIPWNLERIQPPR, SVPWNLERLT, SVPWNLERLTPPR, SVPWNLERTT, SVPWNLERTTPPR, SVPWNLERIL, SVPWNLERILPPR, SVPWNLERIQ, SVPWNLERIQPPR, SIPWSLERTTPPR, SQPWNLERLT, SQPWNLERLTPPR, SQPWNLERIL, SQPWNLERILPPR, SQPWNLERIQ, SQPWNLERIQPPR, SIPWSLERLT, SIPWSLERLTPPR, SIPWSLERTT, SIPWSLERIL, SIPWSLERILPPR, SIPWSLERIQ, SIPWSLERIQPPR, VQPWSLERTL, VQPWSLERTLPPR, SQPWSLERTL, SQPWSLERTLPPR, VQPWNLERLQ, VQPWNLERLQPPR, VQPWSLERLL, VQPWSLERLLPPR, SVPWSLERLT and SVPWNLERLTPPR.

According to a particularly preferred embodiment of the present invention the at least one peptide comprised in the vaccine of the present invention is selected from the group consisting of SIPWSLERIT, SIPWSLERITPPR, SIPWSLERTTPPR, VIPWNLERILPPR, SVPWNLERIQPPR, SIPWSLERTT, SIPWSLERLT, SIPWNLERLTPPR, SIPWSLERIQ, SIPWSLERIQPPR, VIPWNLERIL and SVPWNLERIQ.

TABLE A

| Amino acid residues | | |
|---|---|---|
| Amino acid | Three letter code | One letter code |
| alanine | ala | A |
| arginine | arg | R |
| asparagine | asn | N |
| aspartic acid | asp | D |
| cysteine | cys | C |
| glutamic acid | glu | E |
| glutamine | gln | Q |
| glycine | gly | G |
| histidine | his | H |
| isoleucine | ile | I |
| leucine | leu | L |
| lysine | lys | K |
| methionine | met | M |
| phenylalanine | phe | F |
| proline | pro | P |
| serine | ser | S |
| threonine | thr | T |
| tryptophan | trp | W |
| tyrosine | tyr | Y |
| valine | val | V |

According to a particularly preferred embodiment at least one peptide (SEQ ID No. 1) comprised in the vaccine of the present invention comprises at its N- and/or C-terminus at least one cysteine residue bound directly or via a spacer sequence thereto.

This cysteine residue may serve as a reactive group in order to bind the peptide to another molecule or a carrier. For instance, this group may be used to bind the peptide to a carrier protein. The cysteine residue can be bound directly to the peptides of the present invention or via a spacer sequence. The spacer sequence comprises preferably at least one, preferably at least two, more preferably at least three, even more preferably at least four, and optionally a maximum of ten, preferably a minimum of five small non-polar amino acid residues such as glycines.

According to a preferred embodiment of the present invention the carrier is selected from the group consisting of keyhole limpet haemocyanin (KLH), CRM (preferably CRM197), tetanus toxoid (TT), diphtheria toxin (DT), protein D or any other protein or peptide containing helper T-cell epitopes.

According to the present invention the peptide is coupled or fused to a pharmaceutically acceptable carrier, preferably KLH (Keyhole Limpet Hemocyanin), CRM, tetanus toxoid, albumin-binding protein, bovine serum albumin, a dendrimer, peptide linkers (or flanking regions) as well as the adjuvant substances described in Singh et al. (Singh et al., Nat. Biotech. 17, (1999): 1075-1081 (in particular those in Table 1 of that document)), and O'Hagan et al. (O'Hagan and Valiante, Nature Reviews, Drug Discovery 2 (9); (2003): 727-735 (in particular the endogenous immunopotentiating compounds and delivery systems described therein)), or mixtures thereof. The conjugation chemistry (e.g. via heterobifunctional compounds such as GMBS and of course also others as described in "Bioconjugate Techniques", Greg T. Hermanson) in this context can be selected from reactions known to the skilled man in the art.

Alternatively it is also possible to fuse the at least one peptide of the present invention to a protein carrier by methods known in the art. Such proteins comprise a peptide as described herein together with an unrelated immunogenic protein. Preferably the immunogenic protein is capable of eliciting a recall response. Examples of such proteins include tetanus, tuberculosis, hepatitis proteins and protein D, a surface protein of the gram-negative bacterium Haemophilus influenza B (WO 91/18926). Preferably a protein D derivative is used which comprises approximately the first third of the protein (e.g., the first N-terminal 100-110 amino acids) and which may be lipidated. Another carrier which may be used to provide fusion proteins may be the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; Gene 43; (1986):265-292). LYTA is an autolysin that specifically degrades certain bonds in the peptidoglycan backbone. Within a preferred embodiment, a repeat portion of LYTA may be incorporated into a fusion protein. A repeat portion is found in the C-terminal region starting at residue 178. A particularly preferred repeat portion incorporates residues 188-305.

According to a preferred embodiment of the present invention the peptide is formulated with an adjuvant, preferably adsorbed to aluminium hydroxide.

The vaccine according to the present invention may be formulated with an adjuvant, preferably a low soluble aluminum composition, in particular aluminum hydroxide. Of course, also adjuvants like MF59, aluminum phosphate, calcium phosphate, cytokines (e.g. IL-2, IL-12, GM-CSF), saponins (e.g. QS21), MDP derivatives, CpG oligonucleotides, LPS, MPL, polyphosphazenes, emulsions (e.g. Freund's, SAF), liposomes, virosomes, iscoms, cochleates, PLG microparticles, poloxamer particles, virus-like particles, heat-labile enterotoxin (LT), cholera toxin (CT), mutant toxins (e.g. LTK63 and LTR72), microparticles and/or polymerized liposomes may be used.

Suitable adjuvants are commercially available as, for example, AS01B, AS02A, AS15, AS-2 and derivatives thereof (GlaxoSmithKline, Philadelphia, PA); CWS, TDM, Leif, aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7 or -12 may also be used as adjuvants.

Preferred adjuvants for use in eliciting a predominantly Th1-type response include, for example, a combination of monophosphoryl lipid A, preferably 3-O-deacylated monophosphoryl lipid A (3D-MPL), optionally with an aluminum salt (see, for example, Ribi et al., immunology and Immunopharmacology of Bacterial Endotoxins, Plenum Publ. Corp., NY, (1986): 407-419; GB 2122204B; GB 2220211; and U.S. Pat. No. 4,912,094). A preferred form of 3D-MPL is an emulsion having a small particle size less than 0.2 mm in diameter, and its method of manufacture is disclosed in WO 94/21292. Aqueous formulations comprising monophosphoryl lipid A and a surfactant have been described in WO 98/43670. Exemplified preferred adjuvants include AS01B (MPL and QS21 in a liposome formulation), 3D-MPL and QS21 in a liposome formulation, AS02A (MPL and QS21 and an oil-in-water emulsion), 3D-MPL and QS21 and an oil-in-water emulsion, and AS 15. MPL adjuvants are disclosed e.g. in U.S. Pat. Nos. 4,436,727; 4,877,611; 4,866,034 and U.S. Pat. No. 4,912,094.

CpG-containing oligonucleotides (in which the CpG dinucleotide is unmethylated) also induce a predominantly Th1 response. CpG is an abbreviation for cytosine-guanosine dinucleotide motifs present in DNA. Such oligonucleotides are well known and are described, for example, in WO 96/02555, WO 99/33488, U.S. Pat. Nos. 6,008,200 and 5,856,462. Immunostimulatory DNA sequences are also described, for example, by Sato et al., Science 273; (1996): 352. CpG when formulated into vaccines is generally administered in free solution together with free antigen (WO 96/02555; McCluskie and Davis, supra) or covalently conjugated to an antigen (WO 98/16247), or formulated with a carrier such as aluminium hydroxide ((Hepatitis surface antigen) Davis et al., supra; Brazolot-Millan et al., PNAS USA, 95(26), (1998):15553-8). CpG is known in the art as being an adjuvant that can be administered by both systemic and mucosal routes (WO 96/02555, EP 0 468 520, Davis et al., J. Immunol, 160(2), (1998):870-876; McCluskie and Davis, J. Immunol., 161(9), (1998):4463-6).

Another preferred adjuvant is a saponin or saponin mimetics or derivatives, preferably QS21 (Aquila Biopharmaceuticals Inc.), which may be used alone or in combination with other adjuvants. For example, an enhanced system involves the combination of a monophosphoryl lipid A and saponin derivative, such as the combination of QS21 and 3D-MPL as described in WO 94/00153, or a less reactogenic composition where the QS21 is quenched with cholesterol as described in WO 96/33739. Other preferred formulations comprise an oil-in-water emulsion and tocopherol. A particularly potent adjuvant formulation involving QS21, 3D-MPL and tocopherol in an oil-in-water emulsion is described in WO 95/17210. Additional saponin adjuvants of use in the present invention include QS7 (described in WO 96/33739 and WO 96/11711) and QS17 (described in U.S. Pat. No. 5,057,540 and EP 0 362 279 B1).

Other preferred adjuvants include Montanide ISA 720 (Seppic, France), SAF (Chiron, California, United States), ISCOMS (CSL), MF-59 (Chiron), the SBAS series of adjuvants (e.g., SBAS-2, AS2', AS2, SBAS-4, or SBAS6, available from GlaxoSmithKline), Detox (Corixa), RC-529 (Corixa, Hamilton, MT) and other amino-alkyl glucosaminide 4-phosphates (AGPs). Further example adjuvants include synthetic MPL and adjuvants based on Shiga toxin B subunit (see WO 2005/112991). It is particularly preferred to use aluminium hydroxide as adjuvant.

The vaccine of the present invention may be administered subcutaneously, intramuscularly, intradermally, intravenously (see e.g. "Handbook of Pharmaceutical Manufacturing Formulations", Sarfaraz Niazi, CRC Press Inc, 2004). Depending on the route of administration, the medicament may comprise respective carriers, adjuvants, and/or excipients.

A vaccine which comprises a peptide of the present invention and the pharmaceutically acceptable carrier may be administered by any suitable mode of application, e.g. intradermally (i.d.), intraperitoneally (i.p.), intramuscularly (i.m.), intranasally, orally, subcutaneously (s.c.), etc. and in any suitable delivery device (O'Hagan et al., Nature Reviews, Drug Discovery 2 (9), (2003), 727-735). The peptides of the present invention are preferably formulated for intradermal, subcutaneous or intramuscular administration. Means and methods for obtaining respective formulations are known to the person skilled in the art (see e.g. "Handbook of Pharmaceutical Manufacturing Formulations", Sarfaraz Niazi, CRC Press Inc, 2004).

According to a preferred embodiment of the present invention the vaccine is used in the treatment and/or prevention of disorders caused by hyperlipidemia, hypercholesterolemia and/or atherosclerosis, preferably cardiovascular diseases, stroke or peripheral vascular diseases in particular in mammals, preferably in humans.

As outlined, the peptides of the present invention are able to induce the formation of antibodies which are able to bind specifically PCSK9. The interaction of the antibodies with PCSK9 leads to the increase of low density lipoprotein receptor in liver hepatocytes in vivo, increased plasma cholesterol uptake and subsequent reduction of the plasma LDL cholesterol levels and thus the overall cholesterol levels.

The disease associated with atherosclerosis is preferably selected from the group consisting of peripheral arterial occlusive disease, coronary heart disease, apoplectic cerebral insultus and stroke.

The terms "diseases associated with hyperlipidemia, hypercholesterolemia and/or atherosclerosis" and "disorders caused by hyperlipidemia, hypercholesterolemia and/or atherosclerosis" refer to diseases which are a consequence of hyperlipidemia, hypercholesterolemia and atherosclerosis. These diseases include among others peripheral arterial occlusive disease, coronary heart disease and apoplectic cerebral insultus (see e.g. Steinberg, D. J Lipid Res 46(2005):179-190 and Steinberg, D. J Lipid Res 47(2006): 1339-1351).

According to a preferred embodiment of the present invention the peptides of the present invention are administered to a mammal or an individual in an amount of 0.1 ng to 10 mg, preferably of 0.5 to 500 µg, more preferably 1 to 100 µg, per immunization. In a preferred embodiment these amounts refer to all peptides (if more than one peptide is used in the vaccine) present in the vaccine. In another preferred embodiment these amounts refer to each single fragment present in the vaccine. It is of course possible to provide a vaccine in which the peptides are present in different or equal amounts. However, the peptide of the present invention may alternatively be administered to a mammal or an individual in an amount of 0.1 ng to 10 mg, preferably 10 ng to 1 mg, in particular 100 ng to 300 µg/kg body weight.

The amount of peptides that may be combined with the carrier materials to produce a single dosage form will vary depending upon the host treated and the particular mode of administration. The dose of the vaccine may vary according to factors such as the disease state, age, sex and weight of the mammal or individual, and the ability of antibody to elicit a desired response in the individual. Dosage regime may be adjusted to provide the optimum therapeutic response. For example, several divided doses may be administered daily or the dose may be proportionally reduced as indicated by the exigencies of the therapeutic situation. The dose of the vaccine may also be varied to provide optimum preventative dose response depending upon the circumstances. For instance, the peptides and vaccine of the present invention may be administered to an individual at intervals of several days, one or two weeks or even months or years depending always on the level of antibodies directed to PCSK9.

In a preferred embodiment of the present invention the peptide/vaccine is applied between 2 and 10, preferably between 2 and 7, even more preferably up to 5 and most preferably up to 4 times. This number of immunizations may lead to a basic immunisation. In a particularly preferred embodiment the time interval between the subsequent vaccinations is chosen to be between 2 weeks and 5 years, preferably between 1 month and up to 3 years, more preferably between 2 months and 1.5 years. An exemplified vaccination schedule may comprise 3 to 4 initial vaccinations over a period of 6 to 8 weeks and up to 6 months. Thereafter the vaccination may be repeated every two to ten years. The repeated administration of the peptide/vaccine of the present invention may maximize the final effect of a therapeutic vaccination.

The vaccine of the present invention may also comprise antigens derived from other proteins which are also involved in the regulation of the LDL and/or HDL levels within a human body. For instance, the PCSK9 fragments of the present invention may be combined with epitopes derived from human CETP protein. The vaccine of the present invention may also comprise antigens derived from a different epitope of the PCSK9 protein.

Typically, the vaccine contains the peptides of the present invention in an amount of 0.5 to 500 µg, preferably 1 to 100 µg and alternatively from 0.1 ng to 10 mg, preferably 10 ng to 1 mg, in particular 100 ng to 100 µg, or, alternatively, e.g. 100 fmol to 10 µmol, preferably 10 pmol to 1 µmol, in particular 100 pmol to 100 nmol. Typically, the vaccine may also contain auxiliary substances, e.g. buffers, stabilizers etc.

Yet another aspect of the present invention relates to a method for treating an individual suffering or at risk to suffer from atherosclerosis or a disease associated with atherosclerosis in the course of which a peptide or vaccine according to the present invention is administered to said individual.

Next to the vaccine of the present invention, the individual to be treated may receive also other active ingredients known to influence the LDL and/or HDL levels in humans and mammals such as statics, fibrates, nicotinic acid, cholesterol uptake inhibitor (e.g. ezetimibe), ApoA1 Milano, delipidated HDL, plant sterols. It is particularly preferred to administers to an individual the vaccine of the present invention together (i.e. at the same time, consecutively etc.) with statins. The vaccine of the present invention can also be combined with methods like LDL apheresis. LDL apheresis is a form of apheresis to eliminate the cholesterol-containing particle low-density lipoprotein (LDL) from the bloodstream. Typically LDL apheresis works by leading venous blood through a column coated with antibodies to apolipoprotein B (the main protein of LDL particles), dextran sulfate or polyacrylate, or by precipitating LDL with heparin at low pH. Respective methods are known to a person skilled in the art.

The term "preventing", as used herein, covers measures not only to prevent the occurrence of disease, such as risk factor reduction, but also to arrest its progress and reduce its consequences once established.

As used herein, the term "treatment" or grammatical equivalents encompasses the improvement and/or reversal of the symptoms of disease. A compound which causes an improvement in any parameter associated with disease when used in the screening methods of the instant invention may thereby be identified as a therapeutic compound. The term "treatment" refers to both therapeutic treatment and prophylactic or preventative measures. For example, those who may benefit from treatment with compositions and methods of the present invention include those already with a disease and/or disorder as well as those in which a disease and/or disorder is to be prevented (e.g., using a prophylactic treatment of the present invention).

Another aspect of the present invention relates to a peptide consisting of an amino acid sequence $X_1X_2X_3WX_4X_5X_6RX_7(X_8)_m(X_9)_n$ (SEQ ID No. 1) as defined above.

The present invention is further illustrated by the following embodiments, figures and example, however, without being restricted thereto.

EMBODIMENTS

1. Vaccine comprising at least one peptide consisting of 9 to 25 amino acid residues having the amino acid sequence $$X_1X_2X_3WX_4X_5X_6RX_7(X_8)_m(X_9)_n, \quad \text{(SEQ ID No. 1)}$$

wherein
$X_1$ is an amino acid residue selected from the group of uncharged amino acid residues, preferably selected from the group consisting of serine, threonine, valine and alanine,
$X_2$ is an amino acid residue selected from the group of uncharged amino acid residues, preferably selected from the group of isoleucine, valine, glycine, glutamine and alanine, more preferably isoleucine, valine, glutamine and alanine.
$X_3$ is an amino acid residue selected from the group of uncharged amino acid residues, preferably selected from the group consisting of proline, threonine, alanine and valine, more preferably praline,
$X_4$ is an amino acid residue selected from the group consisting of asparagine, serine, alanine, glutamine and aspartic acid,
$X_5$ is an amino acid residue selected from the group consisting of leucine, glycine, alanine, tyrosine, aspartic acid, phenylalanine and valine, preferably leucine,
$X_6$ is an amino acid residue selected from the group of hydrophilic, negatively charged amino acid residue, preferably an amino acid residue selected from the group consisting of glutamic acid and aspartic acid,
$X_7$ is an amino acid residue selected from the group of uncharged amino acid residues, preferably selected from the group consisting of isoleucine, leucine, alanine and threonine,
$X_8$ is an amino acid residue selected from the group of uncharged amino acid residues, preferably selected from the group consisting of threonine, leucine, glutamine, alanine and serine,
$X_9$ is $X_{10}X_{11}X_{12}$ or a C-terminal truncated fragment thereof consisting of 1 or 2 amino acid residues,
$X_{10}$ is any amino acid residue, preferably an amino acid residue selected from the group of uncharged amino acid residues, preferably selected from the group consisting of proline, alanine and serine,
$X_{11}$ is any amino acid residue, preferably an amino acid residue selected from the group of uncharged amino acid residues, preferably selected from the group consisting of praline, alanine, valine, threonine and asparagine,
$X_{12}$ is any amino acid residue, preferably an amino acid residue selected from the group consisting of arginine, alanine, lysine, serine, and leucine,
m is 0 or 1,
n is 0 or 1, and
SEQ ID No. 1 is not SIPWNLERITPPR or a C-terminal truncated fragment thereof,
wherein said at least one peptide is coupled or fused to a pharmaceutically acceptable carrier.

2. Vaccine according to embodiment 1, wherein $X_1$ is valine, serine or alanine, preferably valine.
3. Vaccine according to embodiment 1 or 2, wherein $X_2$ is valine, isoleucine or glutamine, preferably valine.
4. Vaccine according to any one of embodiments 1 to 3, wherein $X_3$ is proline, threonine, alanine or valine.
5. Vaccine according to any one of embodiments 1 to 4, wherein $X_4$ is serine or asparagine, preferably serine.
6. Vaccine according to any one of embodiments 1 to 5, wherein $X_6$ is glutamic acid.
7. Vaccine according to any one of embodiments 1 to 6, wherein $X_7$ is leucine, isoleucine or threonine, preferably threonine.
8. Vaccine according to any one of embodiments 1 to 7, wherein $X_8$ is glutamine, threonine or leucine.
9. Vaccine according to any one of embodiments 1 to 8, wherein $X_1X_2X_3$ is selected from the group consisting of TIP, VIP, AIP, SVP, SQP, SAP, SGP, SIT, SIA, SIV and VQP.
10. Vaccine according to any one of embodiments 1 to 9, wherein $X_4X_5X_6$ is selected from the group consisting of SLE, ALE, QLE, DLE, NAE, NGE, NYE, NDE, NFE, NVE and NLD.
11. Vaccine according to any one of embodiments 1 to 10, wherein $X_7(X_8)_m$, m being 1, is selected from the group consisting of LT, TT, AT, IL, IQ, IA, IS, TL, LQ and LL.
12. Vaccine according to any one of embodiments 1 to 11, wherein $X_9$ is selected from the group consisting of PPR, PP, P, APR, SPR, PAR, PVR, PTR, PNR, PPA, PPK, PPS and PPL.
13. Vaccine according to any one of embodiments 1 to 12, wherein the at least one peptide is selected from the group consisting of TIPWNLERIT, TIPWNLERITPPR, VIPWNLERIT, VIPWNLERITPPR, AIPWNLERIT, AIPWNLERITPPR, SVPWNLERIT, SVPWNLERITPPR, SQPWNLERIT, SQPWNLERITPPR, SAPWNLERIT, SAPWNLERITPPR, SGPWNLERITPPR, SGPWNLERIT, SITWNLERIT, SITWNLERITPPR, SIAWNLERIT, SIAWNLERITPPR, SIVWNLERITPPR, SIVWNLERIT, SIPWSLERIT, SIPWSLERITPPR, SIPWALERIT, SIPWALERITPPR, SIPWQLERITPPR, SIPWQLERIT, SIPWDLERITPPR, SIPWDLERIT, SIPWNAERIT, SIPWNAERITPPR, SIPWNGERIT, SIPWNGERITPPR, SIPWNYERIT, SIPWNYERITPPR, SIPWNDERIT, SIPWNDERITPPR, SIPWNFERITPPR, SIPWNVERITPPR, SIPWNLDRITPPR, SIPWNFERIT, SIPWNVERIT, SIPWNLDRIT, SIPWNLERLT, SIPWNLERLTPPR, SIPWNLERTT, SIPWNLERTTPPR, SIPWNLERAT, SIPWNLERATPPR, SIPWNLERIL, SIPWNLERILPPR, SIPWNLERIQ, SIPWNLERIQPPR, SIPWNLERIA, SIPWNLERIAPPR, SIPWNLERISPPR, SIPWNLERIS, SIPWNLERITAPR, SIPWNLERITSPR, SIPWNLERITPAR, SIPWNLERITPVR, SIPWNLERITPTR, SIPWNLERITPNR, SIPWNLERITPPA, SIPWNLERITPPK, SIPWNLERITPPS, SIPWNLERITPPL, VIPWNLERLT, VIPWNLERLTPPR, VIPWNLERTT, VIPWNLERTTPPR, VIPWNLERIL, VIPWNLERILPPR, VIPWNLERIQ, VIPWNLERIQPPR, SVPWNLERLT, SVPWNLERLTPPR, SVPWNLERTT, SVPWNLERTTPPR, SVPWNLERIL, SVPWNLERILPPR, SVPWNLERIQ, SVPWNLERIQPPR, SIPWSLERTTPPR, SQPWNLERLT, SQPWNLERLTPPR, SQPWNLERIL, SQPWNLERILPPR, SQPWNLERIQ, SQPWNLERIQPPR, SIPWSLERLT, SIPWSLERLTPPR, SIPWSLERTT, SIPWSLERIL, SIPWSLERILPPR, SIPWSLERIQ, SIPWSLERIQPPR, VQPWSLERTL, VQPWSLERTLPPR, SQPWSLERTL, SQPWSLERTLPPR, VQPWNLERLQ, VQPWNLERLQPPR, VQPWSLERLL, VQPWSLERLLPPR, SVPWSLERLT and SVPWNLERLTPPR.

14. Vaccine according to any one of embodiments 1 to 13, wherein the at least one peptide is selected from the group consisting of SIPWSLERIT, SIPWSLERITPPR, SIPWSLERTTPPR, VIPWNLERILPPR, SVPWNLERIQPPR, SIPWSLERTT, SIPWSLERLT, SIPWSLERLTPPR, SIPWSLERIQ, SIPWSLERIQPPR, VIPWNLERIL and SVPWNLERIQ.

15. Vaccine according to any one of embodiments 1 to 14, wherein the at least one peptide comprises at its N- and/or C-terminus at least one cysteine residue bound directly or via a spacer sequence thereto.

16. Vaccine according to any one of embodiments 1 to 15, wherein the pharmaceutically acceptable carrier is a protein carrier.

17. Vaccine according to embodiment 16, wherein the protein carrier is selected from the group consisting of keyhole limpet haemocyanin (KLH), tetanus toxoid (TT), protein D or diphtheria toxin (DT), preferably a mutated diphtheria toxin, more preferably CRM197.

18. Vaccine according to any one of embodiments 1 to 17, wherein the compound is formulated with an adjuvant, preferably adsorbed to Alhydrogel.

19. Vaccine according to any one of embodiments 1 to 18 to be used in a method for treating and/or preventing disorders caused by hyperlipidemia, hypercholesterolemia and/or atherosclerosis, preferably cardiovascular diseases, stroke or peripheral vascular diseases.

20. Peptide consisting of an amino acid sequence $X_1X_2X_3WX_4X_5X_6RX_7(X_8)_m(X_9)_n$ (SEQ ID No. 1) as defined in any one of embodiments 1 to 15.

Figure 1B:
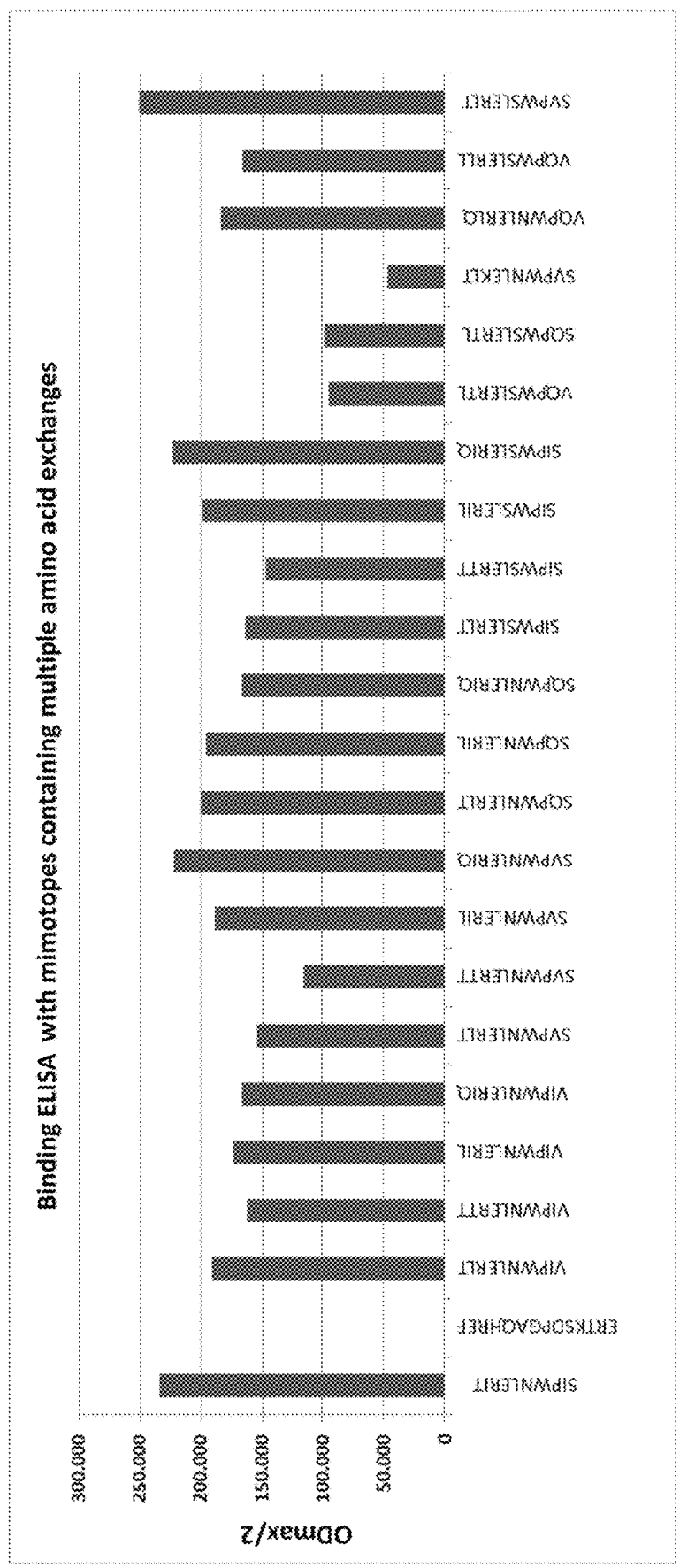

FIGS. 1A and 1B Binding ELISA

FIGS. 1A and 1B show detection of PCSK9 mimotopes sequences by mouse sera containing polyclonal antibodies specific for human PCSK9 aa 153-162 or aa 153-165
A) Mimotopes containing single exchanges
B) Mimotopes containing multiple exchanges The graphs display median titers from all mimotopes compared to the irrelevant negative control. As a positive control the original human PCSK9 sequence is included: aa 153-162 or aa 153-165. Mimotopes with values over 1:50.000 are considered as good candidates.

Figure 2A:
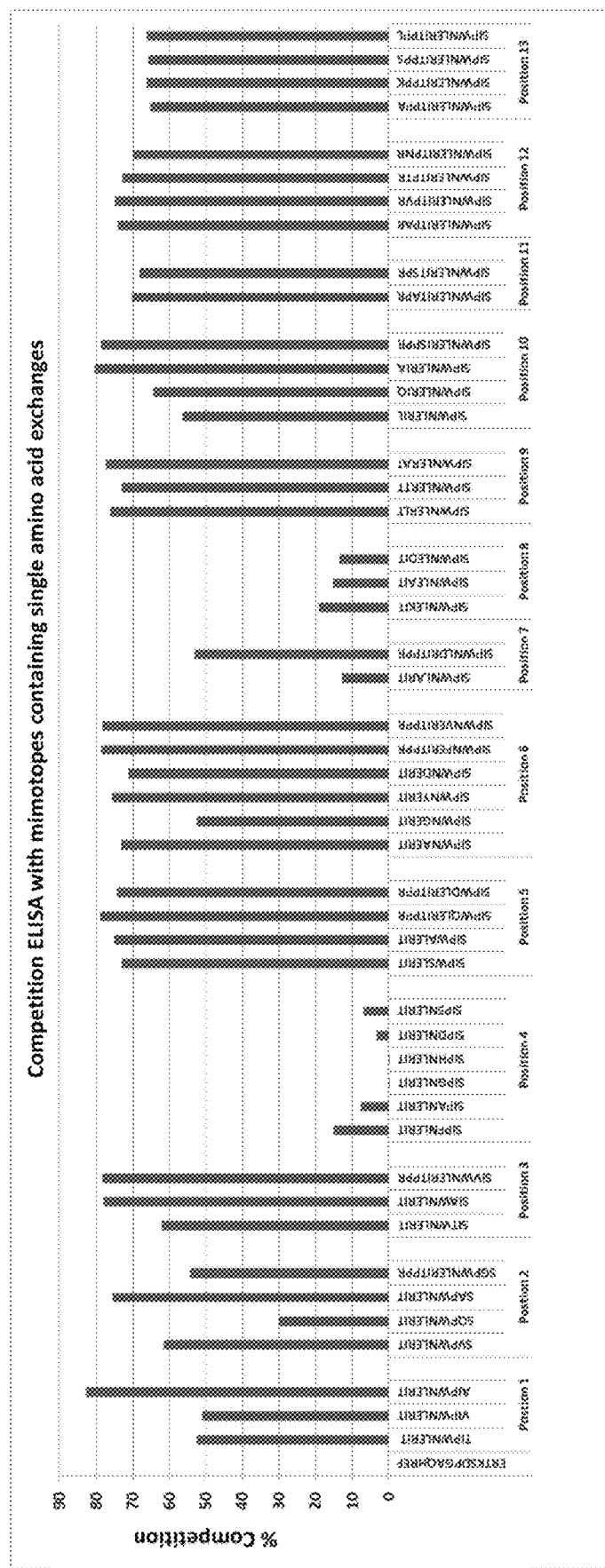
Figure 2B:
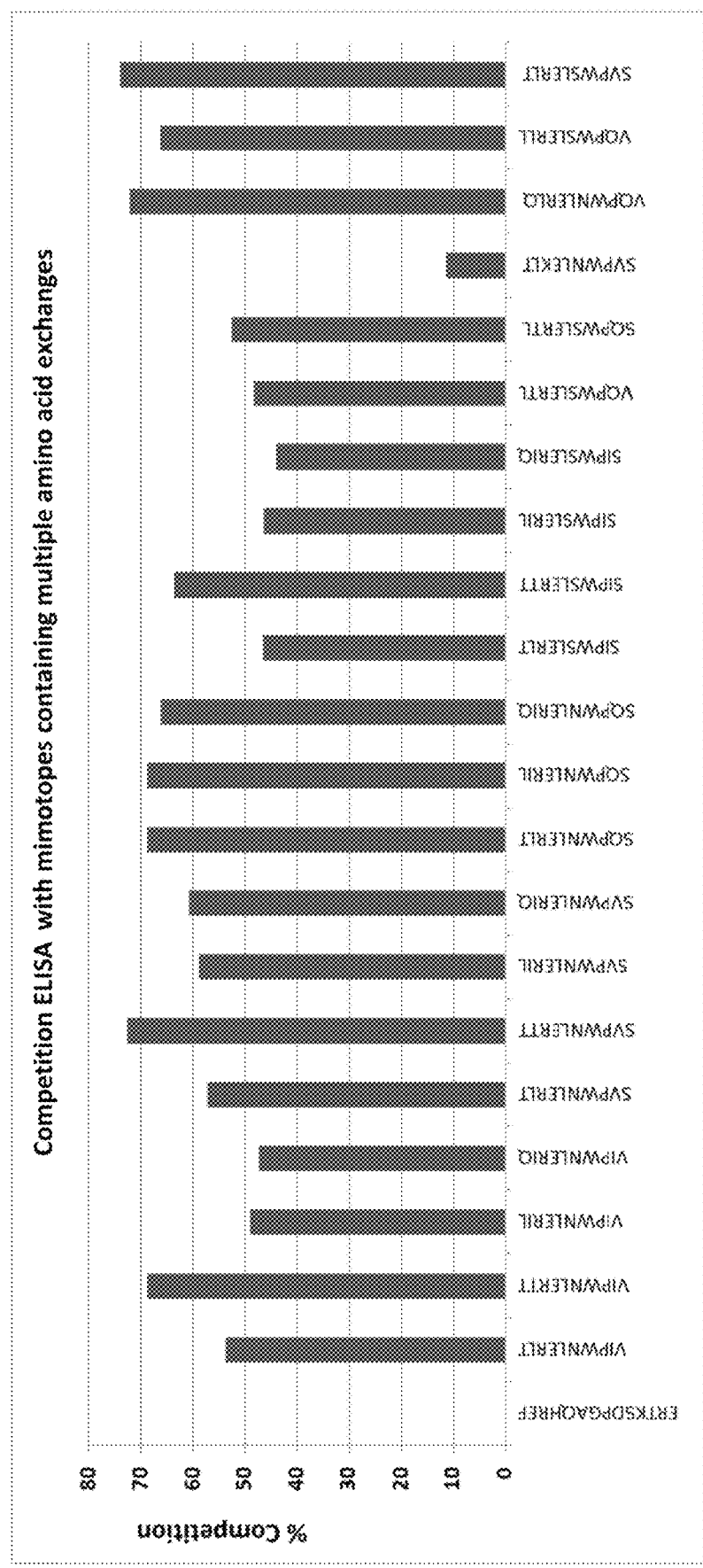

FIGS. 2A and 2B Competition ELISA

FIGS. 2A and 2B show the ability of PCSK9 mimotopes to compete with the original PCSK9 sequence (aa 153-162 or aa 153-165) for binding polyclonal antibodies in mouse sera raised specifically against the latter.

All mimotopes are compared to the negative group (0% competition by an irrelevant peptide). As a positive control for each competition ELISA the original PCSK9 sequences were used (aa 153-162 or aa 153-165).
A) Mimotopes containing single exchanges
B) Mimotopes containing multiple exchanges The graphs display the ability (in percent) of the mimotopes to compete with the original PCSK9 sequence (aa 153-162 or aa 153-165) for binding polyclonal antibodies raised against the latter.

Mimotopes with competition ability over 20% are considered as good candidates.

Figure 3:
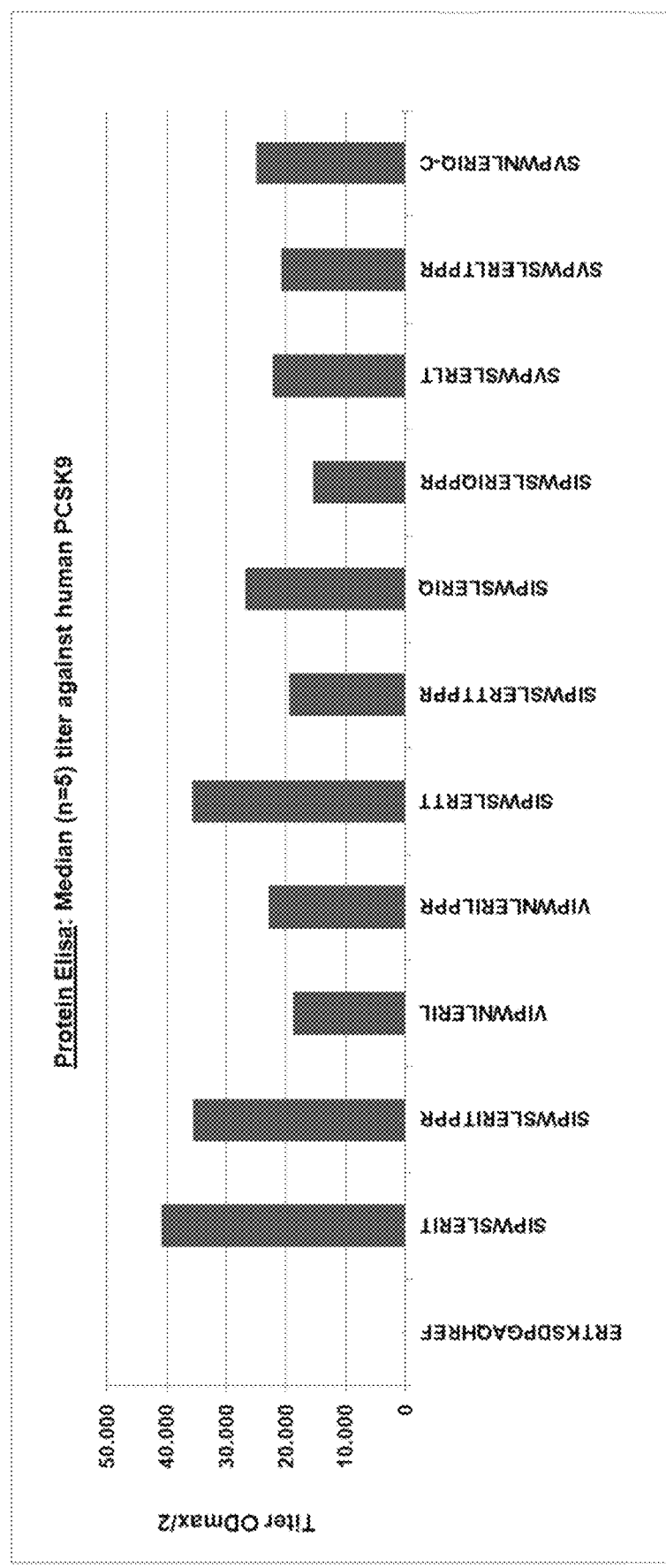

FIG. 3 Protein ELISA

FIG. 3 shows comparison of the median titers (n=5 mice/group) against human PCSK9 protein induced by the indicated sequences. The data reveal the ability of the mimotopes to induce antibodies cross-reacting with human PCSK9 protein. Antibodies raised by irrelevant peptide do not recognize the protein.

Figure 4:
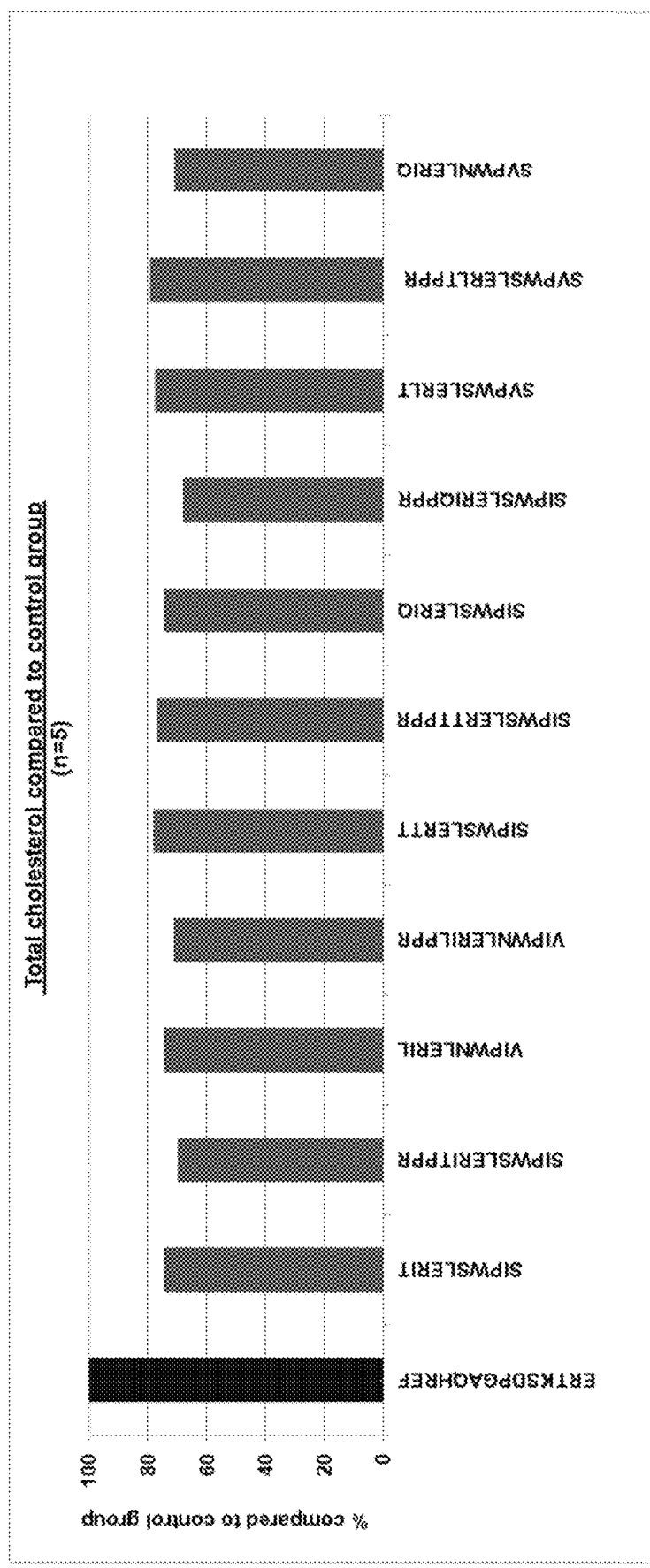

FIG. 4 Total Cholesterol (% Compared to Control Group)

FIG. 4 shows comparison of the mean (n=5 mice/group) total cholesterol levels of mice immunized with mimotopes in comparison to a control group immunized with irrelevant peptide. The data reveal the ability of the mimotopes to substantially lower the levels of total cholesterol in mice up to approximately 30%.

Figures 5A, 5B:
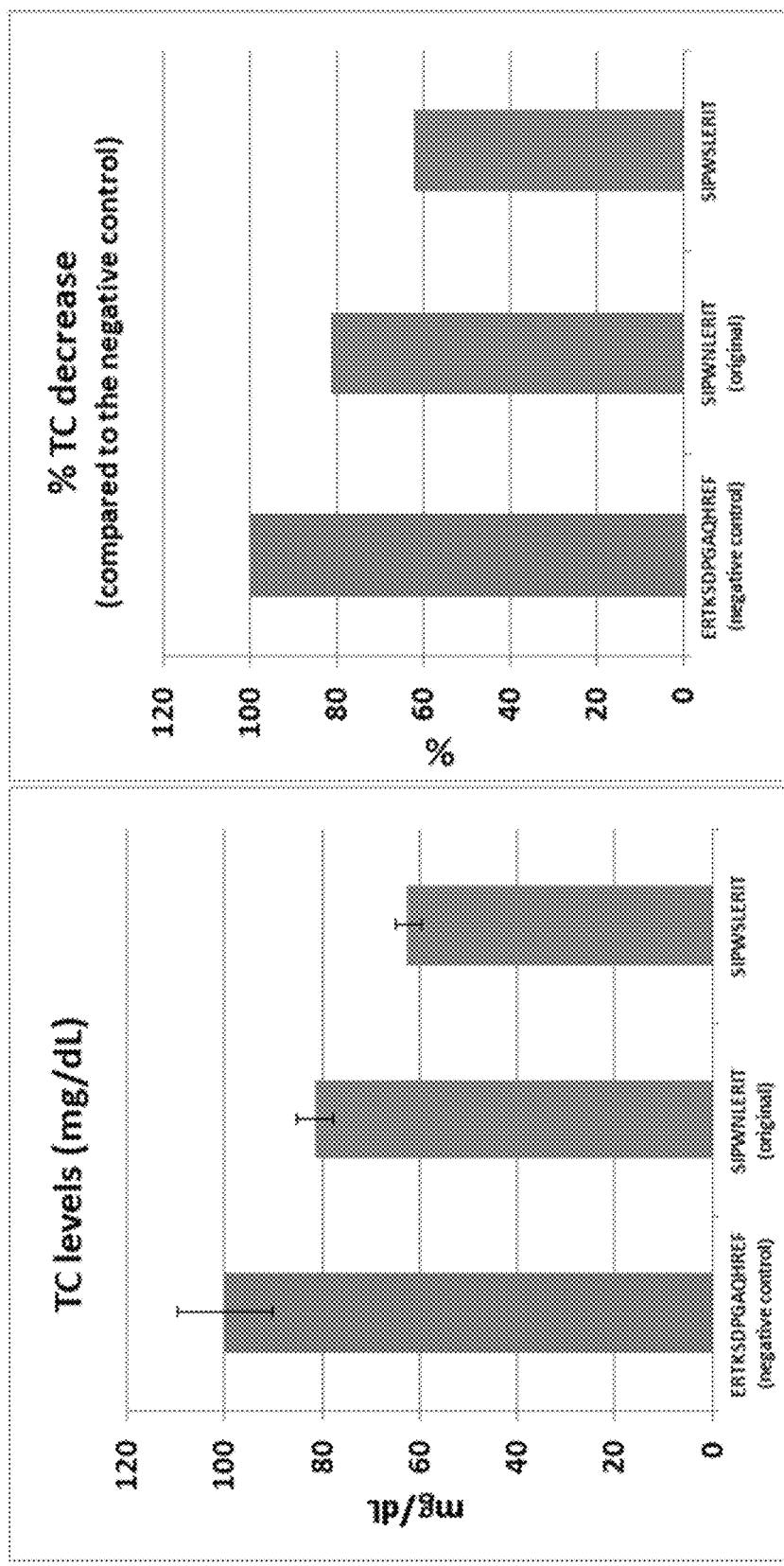

FIGS. 5A and 5B Total Cholesterol (TC) Levels Upon Vaccination

FIGS. 5A and 5B show total cholesterol (TC) levels upon vaccination with original PCSK9 sequence SIPWNLERIT and novel sequence SIPWSLERIT (direct comparison).

Figure 6A:
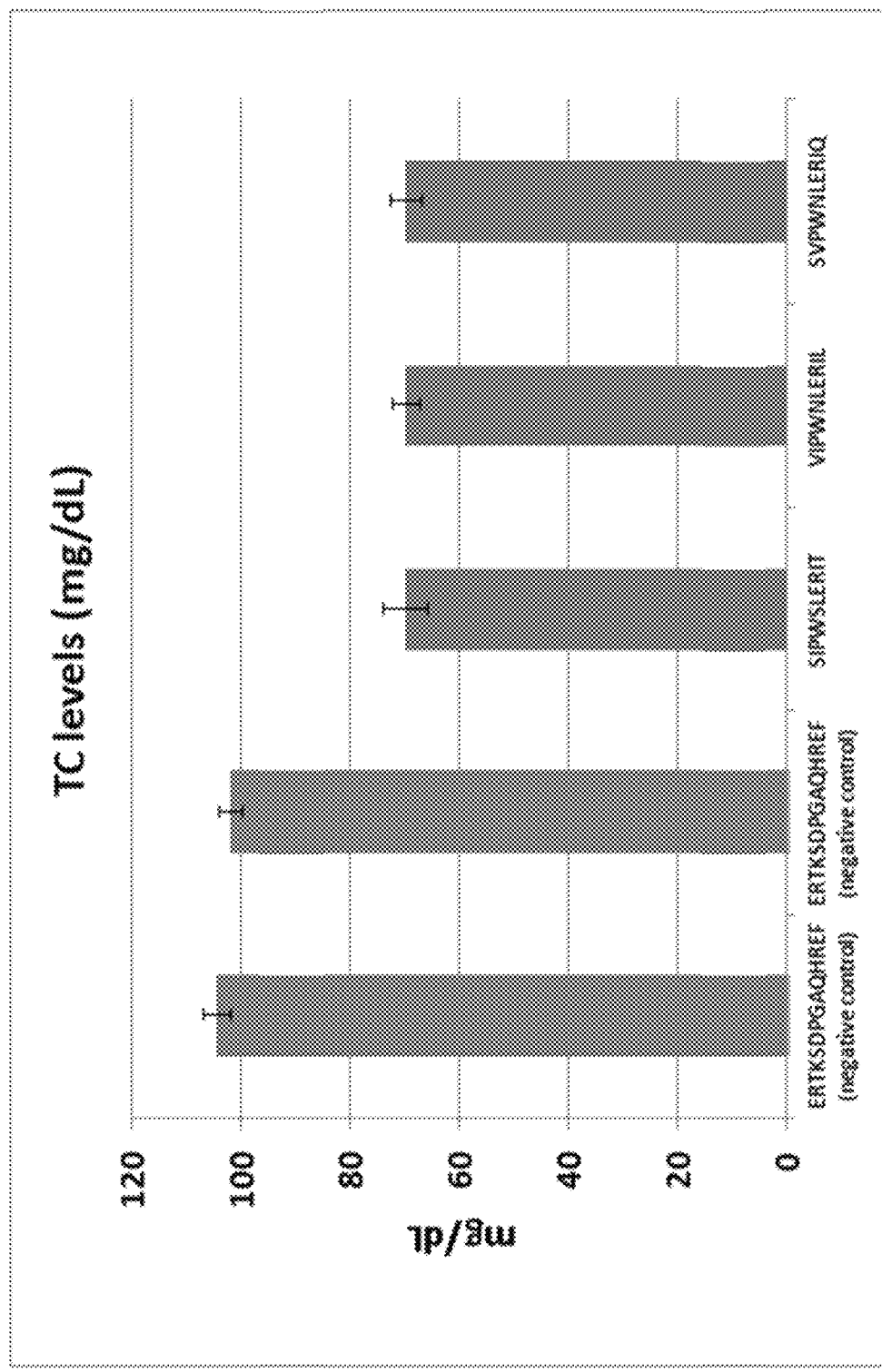
Figure 6B:
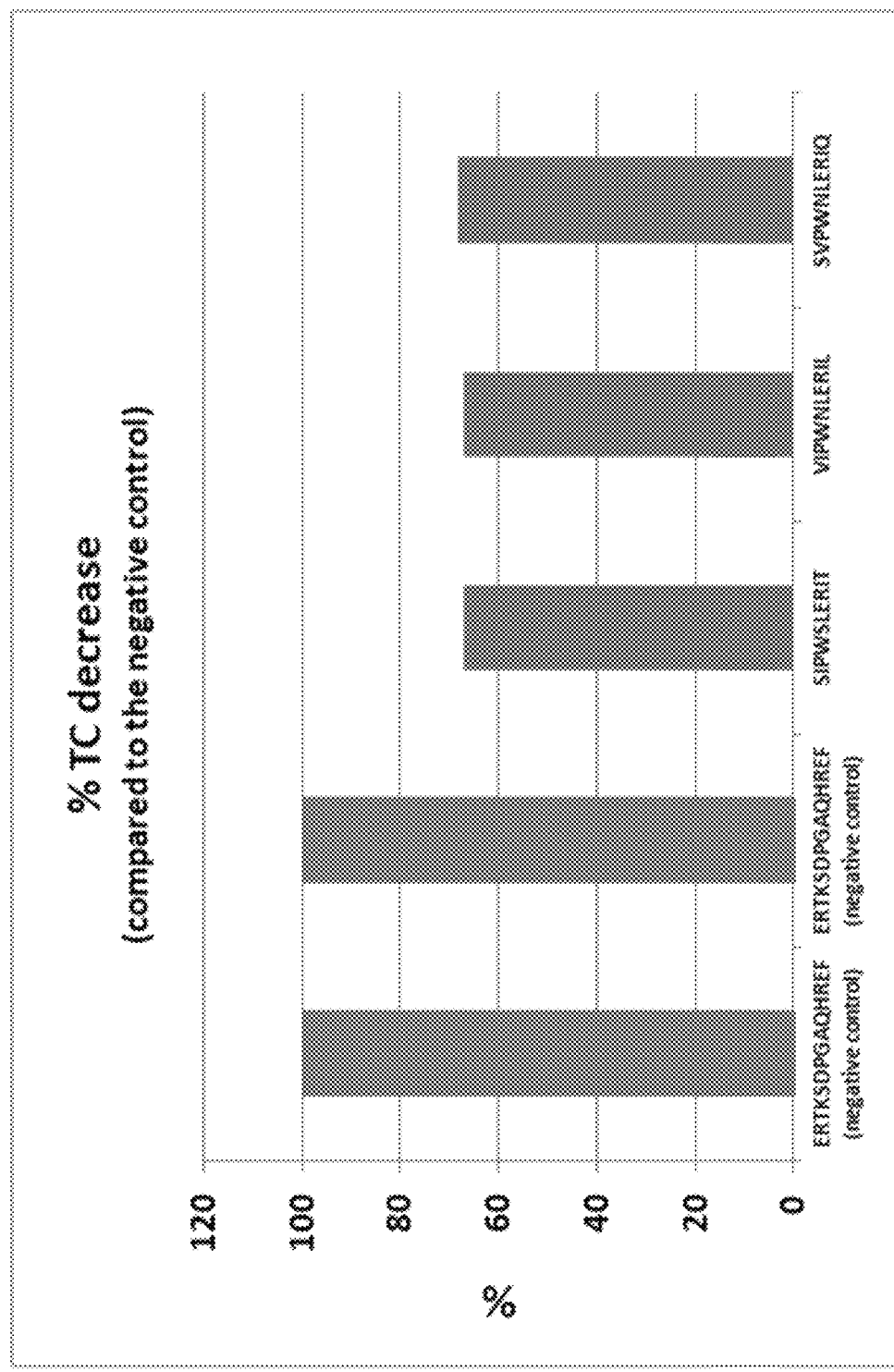

FIGS. 6A and 6B Total Cholesterol (TC) Levels Upon Immunization

FIGS. 6A and 6B show total cholesterol (TC) levels upon immunization with vaccines containing the novel sequences SIPWSLERIT, VIPWNLERIL and SVPWNLERIQ.

EXAMPLES

Materials and Methods

Vaccine

The peptides were conjugated via the heterobifunctional linker GMBS (4-Maleimidobutyric acid N-hydroxysuccinimide ester) to KLH (Keyhole Limpet Hemocyanin).

Animal Experiments

5 Balb/c mice were subcutaneously immunized. Mice had access to food and water ad libitum and were kept under a 12 h light/dark cycle. The age of mice at the beginning of experiments was 8 to 10 weeks.

Mice were injected four times in 2 week intervals with 15 μg of net peptide coupled to KLH and adsorbed to Alhydrogel as adjuvant in a volume of 1 ml in total.

Blood was taken approximately 2 weeks after the final injection.

Competition ELISA

20 µg of each indicated peptide was incubated with sera from mice injected with original PCSK9 sequence (aa 153-162 or aa 153-165: SEQ ID No. 2). Sera were then incubated on ELISA plates coated with the original PCSK9 sequence (aa 153-162 or aa 153-165: SEQ ID No. 2). Detection was performed with anti-mouse IgG antibodies, ABTS was used as a chromogenic substrate and optical density (OD) was measured at 405 nm.

Mimotopes diminishing >20% subsequent binding of the polyclonal antibodies from the sera to the original human PCSK9 epitope (aa 153-162 or 153-165: SEQ ID No.3) coated on the ELISA plates were considered as competing mimotopes and as good candidates.

Binding ELISA

Mimotopes were coated on ELISA plates at a concentration of 1 µmol/mL. After blocking unspecific binding (1% BSA in PBS) appropriate dilutions of sera from mice injected with the original human PCSK9 sequence aa 153-162 or aa 153-165 (SEQ ID No.3) were added and incubated for approximately 1 hour. Subsequently, detection with anti-mouse IgG antibodies was performed. ABTS was used as substrate. OD measurements were performed at 405 nm and titers were defined as the dilution of the serum where 50% of the ODmax is reached.

Protein ELISA

To determine the immunogenicity of the vaccines, ELISA plates were coated with recombinantly expressed human PCSK9 protein. Unspecific binding was blocked by incubation with blocking buffer (1% BSA in PBS). Appropriate serum dilutions were added to the wells, serially diluted 1:2 fold and incubated for approximately 1 hour. Bound antibodies were detected by incubation with anti-mouse IgG antibody, ABTS was added as substrate and the OD at 405 nm was measured. As negative control sera from the control group injected with an irrelevant peptide were analyzed. The titers were defined as the dilution of the serum where 50% of the ODmax in the assay is reached.

Total Cholesterol Assay

Total cholesterol was measured with the LabAssay™ Cholesterol Kit (Wake).

Results

Example 1

List of sequences and median antibody titers against original human PCSK9 sequence (See FIGS. 1A and 1B) and competition capacity (in percent) of the mimotopes, compared to the negative control group (See FIGS. 2A and 2B). In order to facilitate coupling of the peptides to KLH the peptides may comprise a cysteine residue as a linker at the C-terminus.

| Seq ID | Sequence | Median Titer Binding ELISA (ODmax/2) | % Competition compared to the related control group |
|---|---|---|---|
| 1 | $X_1X_2X_3WX_4X_5X_6RX_7(X_8)_m(X_9)_n$ | | |
| 2 | SIPWNLERITPPR | | |
| 3 | ERTKSDPGAQHREF (negative control) | | 0 |
| 4 | ITELSRWPNI (negative control) | | 0 |
| 5 | TIPWNLERIT | 198,000 | 52 |
| 6 | VIPWNLERIT | 152,000 | 51 |
| 7 | AIPWNLERIT | 199,000 | 83 |
| 8 | SVPWNLERIT | 197,000 | 62 |
| 9 | SQPWNLERIT | 149,000 | 30 |
| 10 | SAPWNLERIT | 131,000 | 76 |
| 11 | SGPWNLERITPPR | 81,000 | 54 |
| 12 | SITWNLERIT | 124,000 | 62 |
| 13 | SIAWNLERIT | 147,000 | 78 |
| 14 | SIVWNLERITPPR | 146,000 | 78 |
| 15 | SIPFNLERIT | 42,000 | 15 |
| 16 | SIPANLERIT | 22,000 | 8 |
| 17 | SIPGNLERIT | 21,000 | 0 |
| 18 | SIPHNLERIT | 23,000 | 0 |

-continued

| Seq ID | Sequence | Median Titer Binding ELISA (ODmax/2) | % Competition compared to the related control group |
|---|---|---|---|
| 19 | SIPDNLERIT | 23,000 | 3 |
| 20 | SIPSNLERIT | 22,000 | 7 |
| 21 | SIPWSLERIT | 147,000 | 73 |
| 22 | SIPWALERIT | 157,000 | 75 |
| 23 | SIPWQLERITPPR | 224,000 | 79 |
| 24 | SIPWDLERITPPR | 231,000 | 74 |
| 25 | SIPWNAERIT | 156,000 | 73 |
| 26 | SIPWNGERIT | 56,000 | 52 |
| 27 | SIPWNYERIT | 115,000 | 76 |
| 28 | SIPWNDERIT | 131,000 | 71 |
| 29 | SIPWNFERITPPR | 186,000 | 79 |
| 30 | SIPWNVERITPPR | 197,000 | 78 |
| 31 | SIPWNLARIT | 34,000 | 13 |
| 32 | SIPWNLDRITPPR | 151,000 | 53 |
| 33 | SIPWNLEKIT | 59,000 | 19 |
| 34 | SIPWNLEAIT | 54,000 | 15 |
| 35 | SIPIPINLEDIT | 48,000 | 13 |
| 36 | SIPIPINLERLT | 192,000 | 76 |
| 37 | SIPIPINLERTT | 177,000 | 73 |
| 38 | SIPIPINLERAT | 149,000 | 77 |
| 39 | SIPIPINLERIL | 168,000 | 56 |
| 40 | SIPWNLERIQ | 181,000 | 64 |
| 41 | SIPWNLERIA | 189,000 | 80 |
| 42 | SIPWNLERISPPR | 219,000 | 79 |
| 43 | SIPWNLERITAPR | 226,000 | 70 |
| 44 | SIPWNLERITSPR | 153,000 | 68 |
| 45 | SIPWNLERITPAR | 184,000 | 74 |
| 46 | SIPWNLERITPVIR | 265,000 | 75 |
| 47 | SIPWNLERITPTR | 155,000 | 73 |
| 48 | SIPWNLERITPNR | 186,000 | 70 |
| 49 | SIPWNLERITPPA | 163,000 | 65 |
| 50 | SIPWNLERITPPK | 158,000 | 66 |
| 51 | SIPWNLERITPPS | 149,000 | 66 |
| 52 | SIPWNLERITPPL | 139,000 | 66 |
| 53 | VIPWNLERLT | 191,000 | 54 |
| 54 | VIPWNLERTT | 162,000 | 69 |
| 55 | VIPWNLERIL | 173,000 | 49 |

-continued

| Seq ID | Sequence | Median Titer Binding ELISA (ODmax/2) | % Competition compared to the related control group |
|---|---|---|---|
| 56 | VIPWNLERIQ | 166,000 | 47 |
| 57 | SVPWNLERLT | 154,000 | 57 |
| 58 | SVPWNLERTT | 116,000 | 73 |
| 59 | SVPWNLERIL | 188,000 | 59 |
| 60 | SVPWNLERIQ | 222,000 | 61 |
| 61 | SQPIAINLERLT | 200,000 | 69 |
| 62 | SQPIAINLERIL | 196,000 | 69 |
| 63 | SQPIAINLERIQ | 167,000 | 66 |
| 64 | SIPIAISLERLT | 164,000 | 46 |
| 65 | SIPIAISLERTT | 147,000 | 64 |
| 66 | SIPWSLERIL | 199,000 | 46 |
| 67 | SIPWSLERIQ | 223,000 | 44 |
| 68 | VQPWSLERTL | 95,000 | 48 |
| 69 | SQPWSLERTL | 98,000 | 53 |
| 70 | SVPINNLEKLT | 47,000 | 11 |
| 71 | VQPINNLERLQ | 184,000 | 72 |
| 72 | VQPIAISLERLL | 166,000 | 66 |
| 73 | SVPWSLERLT | 251,000 | 74 |

Example 2

Unexpected Effect of the Peptides According to the Present Invention

In a further experiment, the functionality of the antibodies raised upon immunization with the peptide vaccines according to the present invention is investigated. In the present experiment, the highly significant functionality of the antibodies raised upon immunization with vaccines containing the novel sequences (SEQ ID No.21 SIPWSLERIT, SEQ ID No. 55 VIPWNLERIL and SEQ ID No. 60 SVPWNLERIQ) is demonstrated in comparison to the antibodies raised upon vaccination with vaccines containing the original PCSK9 sequence (SIPWNLERIT) and a negative control sequence—all coupled to the same carrier KLH (FIGS. 5A and 5B and FIGS. 6A and 6B).

For this purpose mice have been immunized with HPLC purified peptides coupled to KLH and formulated with an adjuvant (Alum) as vaccines (Sequence-KLH/Alum). In the first experiment, a direct comparison between the original PCSK9 sequence and the novel sequence SIPWSLERIT has been performed. Here, mice have been immunized with irrelevant peptide vaccine (irrelevant peptide-KLH/Alum) as a negative control group, original PCSK9 sequence vaccine (SIPWNLERIT-KLH/Alum) and the novel sequence vaccine (SIPWSLERIT-KLH/Alum). The latter group (SIPWSLERIT-KLH/Alum) has been used not only to compare its functionality of the induced antibodies to the functionality of the antibodies generated using the original PCSK9 sequence vaccine (SIPWNLERIT-KLH/Alum), but also as a bridging group between different experiments. As it is shown, both vaccines—the original PCSK9 sequence vaccine (SIPWNLERIT-KLH/Alum) and the novel sequence vaccine (SIPWSLERIT-KLH/Alum) are able to strongly reduce the levels of total cholesterol in comparison to the negative control group (FIGS. 5A and 5B). However interestingly, upon vaccination with the novel sequence vaccine (SIPWSLERIT-KLH/Alum), mice show a significant reduction of total cholesterol, compared not only to the negative control group but in fact, compared also to the group injected with vaccines containing the original PCSK9 sequence SIPWNLERIT (FIGS. 5A and 5B).

Subsequently, a second experiment has been performed wherein mice have been immunized with irrelevant peptide as a negative control group and all the three novel sequences SIPWSLERIT, VIPWNLERIL and SVPWNLERIQ, all coupled to KLH and formulated as vaccines. As it has been already mentioned above, the mice immunized with the novel sequence (SIPWSLERIT-KLH/Alum) have been used as a bridging group between the experiments. In fact, the bridging group injected with the novel sequence (SIPWSLERIT-KLH/Alum) is behaving in a similar way in both experiments (FIGS. 5A, 5B, 6A and 6B) and most importantly, all three groups immunized with vaccines containing one of the sequences SIPWSLERIT, VIPWNLERIL or SVPWNLERIQ behave in a very similar way in terms of reduction of plasma total cholesterol levels (FIGS. 6A and 6B).

Thus, the present data confirm the significant efficiency of the vaccines according to the present invention, especially the peptide vaccines containing the sequences SEQ ID No.21 SIPWSLERIT, SEQ ID No. 55 VIPWNLERIL and SEQ ID No. 60 SVPWNLERIQ, to induce functional antibodies that are able not only strongly to decrease the levels of plasma TC compared to the irrelevant negative control, but also to significantly reduce the total cholesterol levels in comparison to a vaccine containing the original PCSK9 sequence (SIPWNLERIT-KLH/Alum).

FIG. 5A shows the plasma mean values in mg/dl upon immunization with vaccine containing the novel sequence SIPWSLERIT, compared to immunization with vaccine containing the original PCSK9 sequence SIPWNLERIT and to the irrelevant (negative) control group (SEQ ID No. 2 ERTKSDPGAQHREF). The highly significant reduction of the TC levels in the group immunized with vaccine containing the novel sequence SIPWSLERIT, compared on one side to vaccine containing the original PCSK9 sequence SIPWNLERIT and on the other side to the negative control group, is evident from this figure. FIG. 5B provides the % decrease of TC of the groups, compared to the irrelevant (negative) control group. Specific attention should be given to the ~20% reduction of TC upon vaccination with the original PCSK9 sequence (SIPWNLERIT-KLH/Alum), compared to the irrelevant negative control and the very strong up to 35-40% reduction in TC levels upon vaccination with the novel sequence (SIPWSLERIT-KLH/Alum).

FIG. 6A shows the plasma mean values in mg/dl upon immunization with vaccines containing the novel sequences SIPWSLERIT, VIPWNLERIL and SVPWNLERIQ, compared to the irrelevant (negative) control group (SEQ ID No. 2 ERTKSDPGAQHREF). The highly significant reduction of the TC levels in all three groups immunized with the novel sequences in comparison to the negative control group, is evident from this figure. FIG. 6B provides the decrease of TC of the groups injected with SIPWSLERIT, VIPWNLERIL and SVPWNLERIQ, compared to the irrelevant (negative) control group. Specific attention should be given to the significantly strong—up to 40% reduction of TC upon vaccination with all three novel sequences SIPWSLERIT, VIPWNLERIL and SVPWNLERIQ. In fact, the group immunized with vaccine containing the novel sequence SIPWSLERIT (bridging group between experiments) has behaved in a similar way in both experiments (see FIGS. 5A and 5B), confirming the significantly higher functionality of the antibodies generated upon immunizations with vaccines containing the novel sequences SIPWSLERIT, VIPWNLERIL and SVPWNLERIQ, in comparison to vaccines containing the original PCSK9 sequence SIPWNLERIT.

From these data it is evident that the vaccines according to the present invention, especially the peptide vaccines comprising the sequences SEQ ID No.21 SIPWSLERIT, SEQ ID No. 55 VIPWNLERIL and SEQ ID No. 60 SVPWNLERIQ show an unexpected and surprisingly advantageous effect compared to the vaccines presented in the prior art.

The invention claimed is:

1. A vaccine comprising at least one peptide, wherein the at least one peptide is selected from the group consisting of TIPWNLERIT (SEQ ID NO: 5), VIPWNLERIT (SEQ ID NO: 6), AIPWNLERIT (SEQ ID NO: 7), SVPWNLERIT (SEQ ID NO: 8), SQPWNLERIT (SEQ ID NO: 9), SAPWNLERIT (SEQ ID NO: 10) SIPWALERIT (SEQ ID NO: 22), SIPWQLERTIPPR (SEQ ID NO: 23), SIPWDLERITPPR (SEQ ID NO: 24), SIPWNLDRITPPR (SEQ ID NO: 32), SIPWNFERIT (amino acids 1-10 of SEQ ID NO: 29), SIPWNVERIT (amino acids 1-10 of SEQ ID NO: 30), SIPWNLDRIT (amino acids 1-10 of SEQ ID NO: 32), SIPWNLERLT (SEQ ID NO: 36), SIPWNLERTT (SEQ ID NO: 37), SIPWNLERAT (SEQ ID NO: 38), SIPWNLERIL (SEQ ID NO: 39), SIPWNLERIQ (SEQ ID NO: 40), SIPWNLERIA (SEQ ID NO: 41), SIPWNLERISPPR (SEQ ID NO: 42), SIPWNLERIS (amino acids 1-10 of SEQ ID NO: 42), SIPWNLERITAPR (SEQ ID NO: 43), SIPWNLERITSPR (SEQ ID NO: 44), SIPWNLERITPAR (SEQ ID NO: 45), SIPWNLERITPVR (SEQ ID NO: 46), SIPWNLERITPTR (SEQ ID NO: 47), SIPWNLERITPNR (SEQ ID NO: 48), SIPWNLERITPPA (SEQ ID NO: 49), SIPWNLERITPPK (SEQ ID NO: 50), SIPWNLERITPPS (SEQ ID NO: 51), SIPWNLERITPPL (SEQ ID NO: 52), VIPWNLERLT (SEQ ID NO: 53), VIPWNLERTT (SEQ ID NO: 54), VIPWNLERIL (SEQ ID NO: 55), VIPWNLERILPPR (SEQ ID NO: 101), VIPWNLERIQ (SEQ ID NO: 56), SVPWNLERLT (SEQ ID NO: 57), SVPWNLERTT (SEQ ID NO: 58), SVPWNLERIL (SEQ ID NO: 59), SVPWNLERIQ (SEQ ID NO: 60), SVPWNLERIQPPR (SEQ ID NO: 106), SIPWSLERTTPPR (SEQ ID NO: 107), SQPWNLERLT (SEQ ID NO: 61), SQPWNLERIL (SEQ ID NO: 62), SQPWNLERIQ (SEQ ID NO: 63), SIPWSLERLT (SEQ ID NO: 64), SIPWSLERTT (SEQ ID NO: 65), SIPWSLERIL (SEQ ID NO: 66), SIPWSLERIQ (SEQ ID NO: 67), VQPWSLERTL (SEQ ID NO: 68), SQPWSLERTL (SEQ ID NO, 69), VQPWNLERLQ (SEQ ID NO: 71), VQPWSLERLL (SEQ ID NO: 72) and SVPWSLERLT (SEQ ID NO: 73).

2. A vaccine comprising at least one peptide, wherein the at least one peptide is selected from the group consisting of SIPWSLERITPPR (SEQ ID NO. 87), SIPWSLERTT (SEQ ID NO. 65), SIPWSLERTTPPR (SEQ ID NO. 107), VIPWNLERIL (SEQ ID NO. 55), VIPWNLERILPPR (SEQ ID NO. 101), SVPWNLERIQ (SEQ ID NO. 60) and SVPWNLERIQPPR (SEQ ID NO. 106).

3. The vaccine according to claim 1, wherein the at least one peptide comprises at its N- and/or C-terminus at least one cysteine residue bound directly or via a spacer sequence thereto.

4. The vaccine according to claim 1, wherein the pharmaceutically acceptable carrier is a protein carrier.

5. The vaccine according to claim 4, wherein the protein carrier is selected from the group consisting of keyhole limpet haemocyanin (KLH), tetanus toxoid (TT), protein D or diphtheria toxin (DT), preferably a mutated diphtheria toxin, more preferably CRM197.

6. The vaccine according to claim 1, wherein the compound is formulated with an adjuvant or adsorbed to Alhydrogel.

7. The vaccine according to claim 1 to be used in a method for treating and/or preventing disorders caused by hyperlipidemia, hypercholesterolemia and/or atherosclerosis, preferably cardiovascular diseases, stroke or peripheral vascular diseases.

* * * * *

SEQUENCE LISTING

<160> NUMBER OF SEQ ID NOS: 118

<210> SEQ ID NO 1
<211> LENGTH: 11
<212> TYPE: PRT
<213> ORGANISM: Artificial Sequence
<220> FEATURE:
<223> OTHER INFORMATION: Artificial Sequence, Mimotope
<220> FEATURE:
<221> NAME/KEY: MISC_FEATURE
<222> LOCATION: (1)..(1)
<223> OTHER INFORMATION: Xaa is an amino acid residue selected from the
      group of uncharged amino acid residues, preferably selected from
      the group consisting of serine, threonine, valine and alanine
<220> FEATURE:
<221> NAME/KEY: MISC_FEATURE
<222> LOCATION: (2)..(2)
<223> OTHER INFORMATION: Xaa is an amino acid residue selected from the
      group of uncharged amino acid residues, preferably selected from
      the group of isoleucine, valine, glycine, glutamine and alanine,
      more preferably isoleucine, valine, glutamine and alanine
<220> FEATURE:
<221> NAME/KEY: MISC_FEATURE
<222> LOCATION: (3)..(3)
<223> OTHER INFORMATION: Xaa is an amino acid residue selected from the
      group of uncharged amino acid residues, preferably selected from
      the group consisting of proline, threonine, alanine and valine,
      more preferably proline
<220> FEATURE:
<221> NAME/KEY: MISC_FEATURE
<222> LOCATION: (5)..(5)
<223> OTHER INFORMATION: Xaa is an amino acid residue selected from the
      group consisting of asparagine, serine, alanine, glutamine and
      aspartic acid
<220> FEATURE:
<221> NAME/KEY: MISC_FEATURE
<222> LOCATION: (6)..(6)
<223> OTHER INFORMATION: Xaa is an amino acid residue selected from the
      group consisting of leucine, glycine, alanine, tyrosine, aspartic
      acid, phe-nylalanine and valine, preferably leucine
<220> FEATURE:

```
<221> NAME/KEY: MISC_FEATURE
<222> LOCATION: (7)..(7)
<223> OTHER INFORMATION: Xaa is an amino acid residue selected from the
      group of hy-drophilic, negatively charged amino acid residue,
      preferably an amino acid residue selected from the group
      consisting of glutamic acid and aspartic acid
<220> FEATURE:
<221> NAME/KEY: MISC_FEATURE
<222> LOCATION: (9)..(9)
<223> OTHER INFORMATION: Xaa is an amino acid residue selected from the
      group of uncharged amino acid residues, preferably selected from
      the group consisting of isoleucine, leucine, alanine and
      threonine
<220> FEATURE:
<221> NAME/KEY: MISC_FEATURE
<222> LOCATION: (10)..(10)
<223> OTHER INFORMATION: Xaa is an amino acid residue selected from the
      group of uncharged amino acid residues, preferably selected from
      the group consisting of threonine, leucine, glutamine, alanine
      and serine or nil
<220> FEATURE:
<221> NAME/KEY: MISC_FEATURE
<222> LOCATION: (11)..(11)
<223> OTHER INFORMATION: Xaa is X10X11X12 as defined in the patent
      application as filed or a C-terminal truncated fragment thereof
      consisting of 1 or 2 amino acid residues or nil

<400> SEQUENCE: 1

Xaa Xaa Xaa Trp Xaa Xaa Xaa Arg Xaa Xaa Xaa
1               5                   10

<210> SEQ ID NO 2
<211> LENGTH: 13
<212> TYPE: PRT
<213> ORGANISM: Artificial Sequence
<220> FEATURE:
<223> OTHER INFORMATION: PCSK9 fragment

<400> SEQUENCE: 2

Ser Ile Pro Trp Asn Leu Glu Arg Ile Thr Pro Pro Arg
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Artificial Sequence

<400> SEQUENCE: 3

Glu Arg Thr Lys Ser Asp Pro Gly Ala Gln His Arg Glu Phe
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Artificial Sequence

<400> SEQUENCE: 4

Ile Thr Glu Leu Ser Arg Trp Pro Asn Ile
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Artificial Sequence, Mimotope
```

```
<400> SEQUENCE: 5

Thr Ile Pro Trp Asn Leu Glu Arg Ile Thr
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Artificial Sequence, Mimotope

<400> SEQUENCE: 6

Val Ile Pro Trp Asn Leu Glu Arg Ile Thr
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Artificial Sequence, Mimotope

<400> SEQUENCE: 7

Ala Ile Pro Trp Asn Leu Glu Arg Ile Thr
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Artificial Sequence, Mimotope

<400> SEQUENCE: 8

Ser Val Pro Trp Asn Leu Glu Arg Ile Thr
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Artificial Sequence, Mimotope

<400> SEQUENCE: 9

Ser Gln Pro Trp Asn Leu Glu Arg Ile Thr
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Artificial Sequence, Mimotope

<400> SEQUENCE: 10

Ser Ala Pro Trp Asn Leu Glu Arg Ile Thr
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Artificial Sequence, Mimotope

<400> SEQUENCE: 11
```

Ser Gly Pro Trp Asn Leu Glu Arg Ile Thr Pro Pro Arg
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Artificial Sequence, Mimotope

<400> SEQUENCE: 12

Ser Ile Thr Trp Asn Leu Glu Arg Ile Thr
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Artificial Sequence, Mimotope

<400> SEQUENCE: 13

Ser Ile Ala Trp Asn Leu Glu Arg Ile Thr
1               5                   10

<210> SEQ ID NO 14
<211> LENGTH: 13
<212> TYPE: PRT
<213> ORGANISM: Artificial Sequence
<220> FEATURE:
<223> OTHER INFORMATION: Artificial Sequence, Mimotope

<400> SEQUENCE: 14

Ser Ile Val Trp Asn Leu Glu Arg Ile Thr Pro Pro Arg
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Artificial Sequence, Mimotope

<400> SEQUENCE: 15

Ser Ile Pro Phe Asn Leu Glu Arg Ile Thr
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Artificial Sequence, Mimotope

<400> SEQUENCE: 16

Ser Ile Pro Ala Asn Leu Glu Arg Ile Thr
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Artificial Sequence, Mimotope

<400> SEQUENCE: 17

```
Ser Ile Pro Gly Asn Leu Glu Arg Ile Thr
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Artificial Sequence, Mimotope

<400> SEQUENCE: 18

Ser Ile Pro His Asn Leu Glu Arg Ile Thr
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Artificial Sequence, Mimotope

<400> SEQUENCE: 19

Ser Ile Pro Asp Asn Leu Glu Arg Ile Thr
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Artificial Sequence, Mimotope

<400> SEQUENCE: 20

Ser Ile Pro Ser Asn Leu Glu Arg Ile Thr
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Artificial Sequence, Mimotope

<400> SEQUENCE: 21

Ser Ile Pro Trp Ser Leu Glu Arg Ile Thr
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Artificial Sequence, Mimotope

<400> SEQUENCE: 22

Ser Ile Pro Trp Ala Leu Glu Arg Ile Thr
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Artificial Sequence, Mimotope

<400> SEQUENCE: 23

Ser Ile Pro Trp Gln Leu Glu Arg Ile Thr Pro Pro Arg
```

```
1               5                   10
```

<210> SEQ ID NO 24
<211> LENGTH: 13
<212> TYPE: PRT
<213> ORGANISM: Artificial Sequence
<220> FEATURE:
<223> OTHER INFORMATION: Artificial Sequence, Mimotope

<400> SEQUENCE: 24

```
Ser Ile Pro Trp Asp Leu Glu Arg Ile Thr Pro Pro Arg
1               5                   10
```

<210> SEQ ID NO 25
<211> LENGTH: 10
<212> TYPE: PRT
<213> ORGANISM: Artificial Sequence
<220> FEATURE:
<223> OTHER INFORMATION: Artificial Sequence, Mimotope

<400> SEQUENCE: 25

```
Ser Ile Pro Trp Asn Ala Glu Arg Ile Thr
1               5                   10
```

<210> SEQ ID NO 26
<211> LENGTH: 10
<212> TYPE: PRT
<213> ORGANISM: Artificial Sequence
<220> FEATURE:
<223> OTHER INFORMATION: Artificial Sequence, Mimotope

<400> SEQUENCE: 26

```
Ser Ile Pro Trp Asn Gly Glu Arg Ile Thr
1               5                   10
```

<210> SEQ ID NO 27
<211> LENGTH: 10
<212> TYPE: PRT
<213> ORGANISM: Artificial Sequence
<220> FEATURE:
<223> OTHER INFORMATION: Artificial Sequence, Mimotope

<400> SEQUENCE: 27

```
Ser Ile Pro Trp Asn Tyr Glu Arg Ile Thr
1               5                   10
```

<210> SEQ ID NO 28
<211> LENGTH: 10
<212> TYPE: PRT
<213> ORGANISM: Artificial Sequence
<220> FEATURE:
<223> OTHER INFORMATION: Artificial Sequence, Mimotope

<400> SEQUENCE: 28

```
Ser Ile Pro Trp Asn Asp Glu Arg Ile Thr
1               5                   10
```

<210> SEQ ID NO 29
<211> LENGTH: 13
<212> TYPE: PRT
<213> ORGANISM: Artificial Sequence
<220> FEATURE:
<223> OTHER INFORMATION: Artificial Sequence, Mimotope

<400> SEQUENCE: 29

```
Ser Ile Pro Trp Asn Phe Glu Arg Ile Thr Pro Pro Arg
1               5                   10
```

```
<210> SEQ ID NO 30
<211> LENGTH: 13
<212> TYPE: PRT
<213> ORGANISM: Artificial Sequence
<220> FEATURE:
<223> OTHER INFORMATION: Artificial Sequence, Mimotope

<400> SEQUENCE: 30

Ser Ile Pro Trp Asn Val Glu Arg Ile Thr Pro Pro Arg
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Artificial Sequence, Mimotope

<400> SEQUENCE: 31

Ser Ile Pro Trp Asn Leu Ala Arg Ile Thr
1               5                   10

<210> SEQ ID NO 32
<211> LENGTH: 13
<212> TYPE: PRT
<213> ORGANISM: Artificial Sequence
<220> FEATURE:
<223> OTHER INFORMATION: Artificial Sequence, Mimotope

<400> SEQUENCE: 32

Ser Ile Pro Trp Asn Leu Asp Arg Ile Thr Pro Pro Arg
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Artificial Sequence, Mimotope

<400> SEQUENCE: 33

Ser Ile Pro Trp Asn Leu Glu Lys Ile Thr
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Artificial Sequence, Mimotope

<400> SEQUENCE: 34

Ser Ile Pro Trp Asn Leu Glu Ala Ile Thr
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Artificial Sequence, Mimotope

<400> SEQUENCE: 35

Ser Ile Pro Trp Asn Leu Glu Asp Ile Thr
1               5                   10
```

```
<210> SEQ ID NO 36
<211> LENGTH: 10
<212> TYPE: PRT
<213> ORGANISM: Artificial Sequence
<220> FEATURE:
<223> OTHER INFORMATION: Artificial Sequence, Mimotope

<400> SEQUENCE: 36

Ser Ile Pro Trp Asn Leu Glu Arg Leu Thr
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Artificial Sequence, Mimotope

<400> SEQUENCE: 37

Ser Ile Pro Trp Asn Leu Glu Arg Thr Thr
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Artificial Sequence, Mimotope

<400> SEQUENCE: 38

Ser Ile Pro Trp Asn Leu Glu Arg Ala Thr
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Artificial Sequence, Mimotope

<400> SEQUENCE: 39

Ser Ile Pro Trp Asn Leu Glu Arg Ile Leu
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Artificial Sequence, Mimotope

<400> SEQUENCE: 40

Ser Ile Pro Trp Asn Leu Glu Arg Ile Gln
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Artificial Sequence, Mimotope

<400> SEQUENCE: 41

Ser Ile Pro Trp Asn Leu Glu Arg Ile Ala
1               5                   10
```

```
<210> SEQ ID NO 42
<211> LENGTH: 13
<212> TYPE: PRT
<213> ORGANISM: Artificial Sequence
<220> FEATURE:
<223> OTHER INFORMATION: Artificial Sequence, Mimotope

<400> SEQUENCE: 42

Ser Ile Pro Trp Asn Leu Glu Arg Ile Ser Pro Pro Arg
1               5                   10

<210> SEQ ID NO 43
<211> LENGTH: 13
<212> TYPE: PRT
<213> ORGANISM: Artificial Sequence
<220> FEATURE:
<223> OTHER INFORMATION: Artificial Sequence, Mimotope

<400> SEQUENCE: 43

Ser Ile Pro Trp Asn Leu Glu Arg Ile Thr Ala Pro Arg
1               5                   10

<210> SEQ ID NO 44
<211> LENGTH: 13
<212> TYPE: PRT
<213> ORGANISM: Artificial Sequence
<220> FEATURE:
<223> OTHER INFORMATION: Artificial Sequence, Mimotope

<400> SEQUENCE: 44

Ser Ile Pro Trp Asn Leu Glu Arg Ile Thr Ser Pro Arg
1               5                   10

<210> SEQ ID NO 45
<211> LENGTH: 13
<212> TYPE: PRT
<213> ORGANISM: Artificial Sequence
<220> FEATURE:
<223> OTHER INFORMATION: Artificial Sequence, Mimotope

<400> SEQUENCE: 45

Ser Ile Pro Trp Asn Leu Glu Arg Ile Thr Pro Ala Arg
1               5                   10

<210> SEQ ID NO 46
<211> LENGTH: 13
<212> TYPE: PRT
<213> ORGANISM: Artificial Sequence
<220> FEATURE:
<223> OTHER INFORMATION: Artificial Sequence, Mimotope

<400> SEQUENCE: 46

Ser Ile Pro Trp Asn Leu Glu Arg Ile Thr Pro Val Arg
1               5                   10

<210> SEQ ID NO 47
<211> LENGTH: 13
<212> TYPE: PRT
<213> ORGANISM: Artificial Sequence
<220> FEATURE:
<223> OTHER INFORMATION: Artificial Sequence, Mimotope

<400> SEQUENCE: 47

Ser Ile Pro Trp Asn Leu Glu Arg Ile Thr Pro Thr Arg
1               5                   10

<210> SEQ ID NO 48
```

```
<211> LENGTH: 13
<212> TYPE: PRT
<213> ORGANISM: Artificial Sequence
<220> FEATURE:
<223> OTHER INFORMATION: Artificial Sequence, Mimotope

<400> SEQUENCE: 48

Ser Ile Pro Trp Asn Leu Glu Arg Ile Thr Pro Asn Arg
1               5                   10

<210> SEQ ID NO 49
<211> LENGTH: 13
<212> TYPE: PRT
<213> ORGANISM: Artificial Sequence
<220> FEATURE:
<223> OTHER INFORMATION: Artificial Sequence, Mimotope

<400> SEQUENCE: 49

Ser Ile Pro Trp Asn Leu Glu Arg Ile Thr Pro Pro Ala
1               5                   10

<210> SEQ ID NO 50
<211> LENGTH: 13
<212> TYPE: PRT
<213> ORGANISM: Artificial Sequence
<220> FEATURE:
<223> OTHER INFORMATION: Artificial Sequence, Mimotope

<400> SEQUENCE: 50

Ser Ile Pro Trp Asn Leu Glu Arg Ile Thr Pro Pro Lys
1               5                   10

<210> SEQ ID NO 51
<211> LENGTH: 13
<212> TYPE: PRT
<213> ORGANISM: Artificial Sequence
<220> FEATURE:
<223> OTHER INFORMATION: Artificial Sequence, Mimotope

<400> SEQUENCE: 51

Ser Ile Pro Trp Asn Leu Glu Arg Ile Thr Pro Pro Ser
1               5                   10

<210> SEQ ID NO 52
<211> LENGTH: 13
<212> TYPE: PRT
<213> ORGANISM: Artificial Sequence
<220> FEATURE:
<223> OTHER INFORMATION: Artificial Sequence, Mimotope

<400> SEQUENCE: 52

Ser Ile Pro Trp Asn Leu Glu Arg Ile Thr Pro Pro Leu
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Artificial Sequence, Mimotope

<400> SEQUENCE: 53

Val Ile Pro Trp Asn Leu Glu Arg Leu Thr
1               5                   10

<210> SEQ ID NO 54
<211> LENGTH: 10
```

<212> TYPE: PRT
<213> ORGANISM: Artificial Sequence
<220> FEATURE:
<223> OTHER INFORMATION: Artificial Sequence, Mimotope

<400> SEQUENCE: 54

Val Ile Pro Trp Asn Leu Glu Arg Thr Thr
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Artificial Sequence, Mimotope

<400> SEQUENCE: 55

Val Ile Pro Trp Asn Leu Glu Arg Ile Leu
1               5                   10

<210> SEQ ID NO 56
<211> LENGTH: 10
<212> TYPE: PRT
<213> ORGANISM: Artificial Sequence
<220> FEATURE:
<223> OTHER INFORMATION: Artificial Sequence, Mimotope

<400> SEQUENCE: 56

Val Ile Pro Trp Asn Leu Glu Arg Ile Gln
1               5                   10

<210> SEQ ID NO 57
<211> LENGTH: 10
<212> TYPE: PRT
<213> ORGANISM: Artificial Sequence
<220> FEATURE:
<223> OTHER INFORMATION: Artificial Sequence, Mimotope

<400> SEQUENCE: 57

Ser Val Pro Trp Asn Leu Glu Arg Leu Thr
1               5                   10

<210> SEQ ID NO 58
<211> LENGTH: 10
<212> TYPE: PRT
<213> ORGANISM: Artificial Sequence
<220> FEATURE:
<223> OTHER INFORMATION: Artificial Sequence, Mimotope

<400> SEQUENCE: 58

Ser Val Pro Trp Asn Leu Glu Arg Thr Thr
1               5                   10

<210> SEQ ID NO 59
<211> LENGTH: 10
<212> TYPE: PRT
<213> ORGANISM: Artificial Sequence
<220> FEATURE:
<223> OTHER INFORMATION: Artificial Sequence, Mimotope

<400> SEQUENCE: 59

Ser Val Pro Trp Asn Leu Glu Arg Ile Leu
1               5                   10

<210> SEQ ID NO 60
<211> LENGTH: 10
<212> TYPE: PRT

<213> ORGANISM: Artificial Sequence
<220> FEATURE:
<223> OTHER INFORMATION: Artificial Sequence, Mimotope

<400> SEQUENCE: 60

Ser Val Pro Trp Asn Leu Glu Arg Ile Gln
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Artificial Sequence, Mimotope

<400> SEQUENCE: 61

Ser Gln Pro Trp Asn Leu Glu Arg Leu Thr
1               5                   10

<210> SEQ ID NO 62
<211> LENGTH: 10
<212> TYPE: PRT
<213> ORGANISM: Artificial Sequence
<220> FEATURE:
<223> OTHER INFORMATION: Artificial Sequence, Mimotope

<400> SEQUENCE: 62

Ser Gln Pro Trp Asn Leu Glu Arg Ile Leu
1               5                   10

<210> SEQ ID NO 63
<211> LENGTH: 10
<212> TYPE: PRT
<213> ORGANISM: Artificial Sequence
<220> FEATURE:
<223> OTHER INFORMATION: Artificial Sequence, Mimotope

<400> SEQUENCE: 63

Ser Gln Pro Trp Asn Leu Glu Arg Ile Gln
1               5                   10

<210> SEQ ID NO 64
<211> LENGTH: 10
<212> TYPE: PRT
<213> ORGANISM: Artificial Sequence
<220> FEATURE:
<223> OTHER INFORMATION: Artificial Sequence, Mimotope

<400> SEQUENCE: 64

Ser Ile Pro Trp Ser Leu Glu Arg Leu Thr
1               5                   10

<210> SEQ ID NO 65
<211> LENGTH: 10
<212> TYPE: PRT
<213> ORGANISM: Artificial Sequence
<220> FEATURE:
<223> OTHER INFORMATION: Artificial Sequence, Mimotope

<400> SEQUENCE: 65

Ser Ile Pro Trp Ser Leu Glu Arg Thr Thr
1               5                   10

<210> SEQ ID NO 66
<211> LENGTH: 10
<212> TYPE: PRT
<213> ORGANISM: Artificial Sequence

```
<220> FEATURE:
<223> OTHER INFORMATION: Artificial Sequence, Mimotope

<400> SEQUENCE: 66

Ser Ile Pro Trp Ser Leu Glu Arg Ile Leu
1               5                   10

<210> SEQ ID NO 67
<211> LENGTH: 10
<212> TYPE: PRT
<213> ORGANISM: Artificial Sequence
<220> FEATURE:
<223> OTHER INFORMATION: Artificial Sequence, Mimotope

<400> SEQUENCE: 67

Ser Ile Pro Trp Ser Leu Glu Arg Ile Gln
1               5                   10

<210> SEQ ID NO 68
<211> LENGTH: 10
<212> TYPE: PRT
<213> ORGANISM: Artificial Sequence
<220> FEATURE:
<223> OTHER INFORMATION: Artificial Sequence, Mimotope

<400> SEQUENCE: 68

Val Gln Pro Trp Ser Leu Glu Arg Thr Leu
1               5                   10

<210> SEQ ID NO 69
<211> LENGTH: 10
<212> TYPE: PRT
<213> ORGANISM: Artificial Sequence
<220> FEATURE:
<223> OTHER INFORMATION: Artificial Sequence, Mimotope

<400> SEQUENCE: 69

Ser Gln Pro Trp Ser Leu Glu Arg Thr Leu
1               5                   10

<210> SEQ ID NO 70
<211> LENGTH: 10
<212> TYPE: PRT
<213> ORGANISM: Artificial Sequence
<220> FEATURE:
<223> OTHER INFORMATION: Artificial Sequence, Mimotope

<400> SEQUENCE: 70

Ser Val Pro Trp Asn Leu Glu Lys Leu Thr
1               5                   10

<210> SEQ ID NO 71
<211> LENGTH: 10
<212> TYPE: PRT
<213> ORGANISM: Artificial Sequence
<220> FEATURE:
<223> OTHER INFORMATION: Artificial Sequence, Mimotope

<400> SEQUENCE: 71

Val Gln Pro Trp Asn Leu Glu Arg Leu Gln
1               5                   10

<210> SEQ ID NO 72
<211> LENGTH: 10
<212> TYPE: PRT
<213> ORGANISM: Artificial Sequence
<220> FEATURE:
```

<223> OTHER INFORMATION: Artificial Sequence, Mimotope

<400> SEQUENCE: 72

Val Gln Pro Trp Ser Leu Glu Arg Leu Leu
1               5                   10

<210> SEQ ID NO 73
<211> LENGTH: 10
<212> TYPE: PRT
<213> ORGANISM: Artificial Sequence
<220> FEATURE:
<223> OTHER INFORMATION: Artificial Sequence, Mimotope

<400> SEQUENCE: 73

Ser Val Pro Trp Ser Leu Glu Arg Leu Thr
1               5                   10

<210> SEQ ID NO 74
<211> LENGTH: 30
<212> TYPE: PRT
<213> ORGANISM: Artificial Sequence
<220> FEATURE:
<223> OTHER INFORMATION: Artificial Sequence, Mimotope

<400> SEQUENCE: 74

Ser Ile Pro Trp Asn Leu Glu Arg Ile Thr Pro Pro Arg Tyr Arg Ala
1               5                   10                  15

Asp Glu Tyr Gln Pro Pro Asp Gly Gly Ser Leu Val Glu Val
            20                  25                  30

<210> SEQ ID NO 75
<211> LENGTH: 10
<212> TYPE: PRT
<213> ORGANISM: Artificial Sequence
<220> FEATURE:
<223> OTHER INFORMATION: Artificial Sequence, Mimotope

<400> SEQUENCE: 75

Ser Ile Pro Trp Asn Leu Glu Arg Ile Thr
1               5                   10

<210> SEQ ID NO 76
<211> LENGTH: 9
<212> TYPE: PRT
<213> ORGANISM: Artificial Sequence
<220> FEATURE:
<223> OTHER INFORMATION: Artificial Sequence, Mimotope

<400> SEQUENCE: 76

Ser Ile Pro Trp Asn Leu Glu Arg Ile
1               5

<210> SEQ ID NO 77
<211> LENGTH: 12
<212> TYPE: PRT
<213> ORGANISM: Artificial Sequence
<220> FEATURE:
<223> OTHER INFORMATION: Artificial Sequence, Mimotope

<400> SEQUENCE: 77

Ser Ile Pro Trp Asn Leu Glu Arg Ile Thr Pro Pro
1               5                   10

<210> SEQ ID NO 78
<211> LENGTH: 11
<212> TYPE: PRT

```
<213> ORGANISM: Artificial Sequence
<220> FEATURE:
<223> OTHER INFORMATION: Artificial Sequence, Mimotope

<400> SEQUENCE: 78

Ser Ile Pro Trp Asn Leu Glu Arg Ile Thr Pro
1               5                   10

<210> SEQ ID NO 79
<211> LENGTH: 13
<212> TYPE: PRT
<213> ORGANISM: Artificial Sequence
<220> FEATURE:
<223> OTHER INFORMATION: Artificial Sequence, Mimotope

<400> SEQUENCE: 79

Thr Ile Pro Trp Asn Leu Glu Arg Ile Thr Pro Pro Arg
1               5                   10

<210> SEQ ID NO 80
<211> LENGTH: 13
<212> TYPE: PRT
<213> ORGANISM: Artificial Sequence
<220> FEATURE:
<223> OTHER INFORMATION: Artificial Sequence, Mimotope

<400> SEQUENCE: 80

Val Ile Pro Trp Asn Leu Glu Arg Ile Thr Pro Pro Arg
1               5                   10

<210> SEQ ID NO 81
<211> LENGTH: 13
<212> TYPE: PRT
<213> ORGANISM: Artificial Sequence
<220> FEATURE:
<223> OTHER INFORMATION: Artificial Sequence, Mimotope

<400> SEQUENCE: 81

Ala Ile Pro Trp Asn Leu Glu Arg Ile Thr Pro Pro Arg
1               5                   10

<210> SEQ ID NO 82
<211> LENGTH: 13
<212> TYPE: PRT
<213> ORGANISM: Artificial Sequence
<220> FEATURE:
<223> OTHER INFORMATION: Artificial Sequence, Mimotope

<400> SEQUENCE: 82

Ser Val Pro Trp Asn Leu Glu Arg Ile Thr Pro Pro Arg
1               5                   10

<210> SEQ ID NO 83
<211> LENGTH: 13
<212> TYPE: PRT
<213> ORGANISM: Artificial Sequence
<220> FEATURE:
<223> OTHER INFORMATION: Artificial Sequence, Mimotope

<400> SEQUENCE: 83

Ser Gln Pro Trp Asn Leu Glu Arg Ile Thr Pro Pro Arg
1               5                   10

<210> SEQ ID NO 84
<211> LENGTH: 13
<212> TYPE: PRT
<213> ORGANISM: Artificial Sequence
```

```
<220> FEATURE:
<223> OTHER INFORMATION: Artificial Sequence, Mimotope

<400> SEQUENCE: 84

Ser Ala Pro Trp Asn Leu Glu Arg Ile Thr Pro Pro Arg
1               5                   10

<210> SEQ ID NO 85
<211> LENGTH: 13
<212> TYPE: PRT
<213> ORGANISM: Artificial Sequence
<220> FEATURE:
<223> OTHER INFORMATION: Artificial Sequence, Mimotope

<400> SEQUENCE: 85

Ser Ile Thr Trp Asn Leu Glu Arg Ile Thr Pro Pro Arg
1               5                   10

<210> SEQ ID NO 86
<211> LENGTH: 13
<212> TYPE: PRT
<213> ORGANISM: Artificial Sequence
<220> FEATURE:
<223> OTHER INFORMATION: Artificial Sequence, Mimotope

<400> SEQUENCE: 86

Ser Ile Ala Trp Asn Leu Glu Arg Ile Thr Pro Pro Arg
1               5                   10

<210> SEQ ID NO 87
<211> LENGTH: 13
<212> TYPE: PRT
<213> ORGANISM: Artificial Sequence
<220> FEATURE:
<223> OTHER INFORMATION: Artificial Sequence, Mimotope

<400> SEQUENCE: 87

Ser Ile Pro Trp Ser Leu Glu Arg Ile Thr Pro Pro Arg
1               5                   10

<210> SEQ ID NO 88
<211> LENGTH: 13
<212> TYPE: PRT
<213> ORGANISM: Artificial Sequence
<220> FEATURE:
<223> OTHER INFORMATION: Artificial Sequence, Mimotope

<400> SEQUENCE: 88

Ser Ile Pro Trp Ala Leu Glu Arg Ile Thr Pro Pro Arg
1               5                   10

<210> SEQ ID NO 89
<211> LENGTH: 13
<212> TYPE: PRT
<213> ORGANISM: Artificial Sequence
<220> FEATURE:
<223> OTHER INFORMATION: Artificial Sequence, Mimotope

<400> SEQUENCE: 89

Ser Ile Pro Trp Asn Ala Glu Arg Ile Thr Pro Pro Arg
1               5                   10

<210> SEQ ID NO 90
<211> LENGTH: 13
<212> TYPE: PRT
<213> ORGANISM: Artificial Sequence
<220> FEATURE:
```

```
<223> OTHER INFORMATION: Artificial Sequence, Mimotope

<400> SEQUENCE: 90

Ser Ile Pro Trp Asn Gly Glu Arg Ile Thr Pro Pro Arg
1               5                   10

<210> SEQ ID NO 91
<211> LENGTH: 13
<212> TYPE: PRT
<213> ORGANISM: Artificial Sequence
<220> FEATURE:
<223> OTHER INFORMATION: Artificial Sequence, Mimotope

<400> SEQUENCE: 91

Ser Ile Pro Trp Asn Tyr Glu Arg Ile Thr Pro Pro Arg
1               5                   10

<210> SEQ ID NO 92
<211> LENGTH: 13
<212> TYPE: PRT
<213> ORGANISM: Artificial Sequence
<220> FEATURE:
<223> OTHER INFORMATION: Artificial Sequence, Mimotope

<400> SEQUENCE: 92

Ser Ile Pro Trp Asn Asp Glu Arg Ile Thr Pro Pro Arg
1               5                   10

<210> SEQ ID NO 93
<211> LENGTH: 13
<212> TYPE: PRT
<213> ORGANISM: Artificial Sequence
<220> FEATURE:
<223> OTHER INFORMATION: Artificial Sequence, Mimotope

<400> SEQUENCE: 93

Ser Ile Pro Trp Asn Leu Glu Arg Leu Thr Pro Pro Arg
1               5                   10

<210> SEQ ID NO 94
<211> LENGTH: 13
<212> TYPE: PRT
<213> ORGANISM: Artificial Sequence
<220> FEATURE:
<223> OTHER INFORMATION: Artificial Sequence, Mimotope

<400> SEQUENCE: 94

Ser Ile Pro Trp Asn Leu Glu Arg Thr Thr Pro Pro Arg
1               5                   10

<210> SEQ ID NO 95
<211> LENGTH: 13
<212> TYPE: PRT
<213> ORGANISM: Artificial Sequence
<220> FEATURE:
<223> OTHER INFORMATION: Artificial Sequence, Mimotope

<400> SEQUENCE: 95

Ser Ile Pro Trp Asn Leu Glu Arg Ala Thr Pro Pro Arg
1               5                   10

<210> SEQ ID NO 96
<211> LENGTH: 13
<212> TYPE: PRT
<213> ORGANISM: Artificial Sequence
<220> FEATURE:
<223> OTHER INFORMATION: Artificial Sequence, Mimotope
```

```
<400> SEQUENCE: 96

Ser Ile Pro Trp Asn Leu Glu Arg Ile Leu Pro Pro Arg
1               5                   10

<210> SEQ ID NO 97
<211> LENGTH: 13
<212> TYPE: PRT
<213> ORGANISM: Artificial Sequence
<220> FEATURE:
<223> OTHER INFORMATION: Artificial Sequence, Mimotope

<400> SEQUENCE: 97

Ser Ile Pro Trp Asn Leu Glu Arg Ile Gln Pro Pro Arg
1               5                   10

<210> SEQ ID NO 98
<211> LENGTH: 13
<212> TYPE: PRT
<213> ORGANISM: Artificial Sequence
<220> FEATURE:
<223> OTHER INFORMATION: Artificial Sequence, Mimotope

<400> SEQUENCE: 98

Ser Ile Pro Trp Asn Leu Glu Arg Ile Ala Pro Pro Arg
1               5                   10

<210> SEQ ID NO 99
<211> LENGTH: 13
<212> TYPE: PRT
<213> ORGANISM: Artificial Sequence
<220> FEATURE:
<223> OTHER INFORMATION: Artificial Sequence, Mimotope

<400> SEQUENCE: 99

Val Ile Pro Trp Asn Leu Glu Arg Leu Thr Pro Pro Arg
1               5                   10

<210> SEQ ID NO 100
<211> LENGTH: 13
<212> TYPE: PRT
<213> ORGANISM: Artificial Sequence
<220> FEATURE:
<223> OTHER INFORMATION: Artificial Sequence, Mimotope

<400> SEQUENCE: 100

Val Ile Pro Trp Asn Leu Glu Arg Thr Thr Pro Pro Arg
1               5                   10

<210> SEQ ID NO 101
<211> LENGTH: 13
<212> TYPE: PRT
<213> ORGANISM: Artificial Sequence
<220> FEATURE:
<223> OTHER INFORMATION: Artificial Sequence, Mimotope

<400> SEQUENCE: 101

Val Ile Pro Trp Asn Leu Glu Arg Ile Leu Pro Pro Arg
1               5                   10

<210> SEQ ID NO 102
<211> LENGTH: 13
<212> TYPE: PRT
<213> ORGANISM: Artificial Sequence
<220> FEATURE:
<223> OTHER INFORMATION: Artificial Sequence, Mimotope
```

```
<400> SEQUENCE: 102

Val Ile Pro Trp Asn Leu Glu Arg Ile Gln Pro Pro Arg
1               5                   10

<210> SEQ ID NO 103
<211> LENGTH: 13
<212> TYPE: PRT
<213> ORGANISM: Artificial Sequence
<220> FEATURE:
<223> OTHER INFORMATION: Artificial Sequence, Mimotope

<400> SEQUENCE: 103

Ser Val Pro Trp Asn Leu Glu Arg Leu Thr Pro Pro Arg
1               5                   10

<210> SEQ ID NO 104
<211> LENGTH: 13
<212> TYPE: PRT
<213> ORGANISM: Artificial Sequence
<220> FEATURE:
<223> OTHER INFORMATION: Artificial Sequence, Mimotope

<400> SEQUENCE: 104

Ser Val Pro Trp Asn Leu Glu Arg Thr Thr Pro Pro Arg
1               5                   10

<210> SEQ ID NO 105
<211> LENGTH: 13
<212> TYPE: PRT
<213> ORGANISM: Artificial Sequence
<220> FEATURE:
<223> OTHER INFORMATION: Artificial Sequence, Mimotope

<400> SEQUENCE: 105

Ser Val Pro Trp Asn Leu Glu Arg Ile Leu Pro Pro Arg
1               5                   10

<210> SEQ ID NO 106
<211> LENGTH: 13
<212> TYPE: PRT
<213> ORGANISM: Artificial Sequence
<220> FEATURE:
<223> OTHER INFORMATION: Artificial Sequence, Mimotope

<400> SEQUENCE: 106

Ser Val Pro Trp Asn Leu Glu Arg Ile Gln Pro Pro Arg
1               5                   10

<210> SEQ ID NO 107
<211> LENGTH: 13
<212> TYPE: PRT
<213> ORGANISM: Artificial Sequence
<220> FEATURE:
<223> OTHER INFORMATION: Artificial Sequence, Mimotope

<400> SEQUENCE: 107

Ser Ile Pro Trp Ser Leu Glu Arg Thr Thr Pro Pro Arg
1               5                   10

<210> SEQ ID NO 108
<211> LENGTH: 13
<212> TYPE: PRT
<213> ORGANISM: Artificial Sequence
<220> FEATURE:
<223> OTHER INFORMATION: Artificial Sequence, Mimotope

<400> SEQUENCE: 108
```

Ser Gln Pro Trp Asn Leu Glu Arg Leu Thr Pro Pro Arg
1               5                   10

<210> SEQ ID NO 109
<211> LENGTH: 13
<212> TYPE: PRT
<213> ORGANISM: Artificial Sequence
<220> FEATURE:
<223> OTHER INFORMATION: Artificial Sequence, Mimotope

<400> SEQUENCE: 109

Ser Gln Pro Trp Asn Leu Glu Arg Ile Leu Pro Pro Arg
1               5                   10

<210> SEQ ID NO 110
<211> LENGTH: 13
<212> TYPE: PRT
<213> ORGANISM: Artificial Sequence
<220> FEATURE:
<223> OTHER INFORMATION: Artificial Sequence, Mimotope

<400> SEQUENCE: 110

Ser Gln Pro Trp Asn Leu Glu Arg Ile Gln Pro Pro Arg
1               5                   10

<210> SEQ ID NO 111
<211> LENGTH: 13
<212> TYPE: PRT
<213> ORGANISM: Artificial Sequence
<220> FEATURE:
<223> OTHER INFORMATION: Artificial Sequence, Mimotope

<400> SEQUENCE: 111

Ser Ile Pro Trp Ser Leu Glu Arg Leu Thr Pro Pro Arg
1               5                   10

<210> SEQ ID NO 112
<211> LENGTH: 13
<212> TYPE: PRT
<213> ORGANISM: Artificial Sequence
<220> FEATURE:
<223> OTHER INFORMATION: Artificial Sequence, Mimotope

<400> SEQUENCE: 112

Ser Ile Pro Trp Ser Leu Glu Arg Ile Leu Pro Pro Arg
1               5                   10

<210> SEQ ID NO 113
<211> LENGTH: 13
<212> TYPE: PRT
<213> ORGANISM: Artificial Sequence
<220> FEATURE:
<223> OTHER INFORMATION: Artificial Sequence, Mimotope

<400> SEQUENCE: 113

Ser Ile Pro Trp Ser Leu Glu Arg Ile Gln Pro Pro Arg
1               5                   10

<210> SEQ ID NO 114
<211> LENGTH: 13
<212> TYPE: PRT
<213> ORGANISM: Artificial Sequence
<220> FEATURE:
<223> OTHER INFORMATION: Artificial Sequence, Mimotope

<400> SEQUENCE: 114

```
Val Gln Pro Trp Ser Leu Glu Arg Thr Leu Pro Pro Arg
1               5                   10
```

```
<210> SEQ ID NO 115
<211> LENGTH: 13
<212> TYPE: PRT
<213> ORGANISM: Artificial Sequence
<220> FEATURE:
<223> OTHER INFORMATION: Artificial Sequence, Mimotope

<400> SEQUENCE: 115

Ser Gln Pro Trp Ser Leu Glu Arg Thr Leu Pro Pro Arg
1               5                   10

<210> SEQ ID NO 116
<211> LENGTH: 13
<212> TYPE: PRT
<213> ORGANISM: Artificial Sequence
<220> FEATURE:
<223> OTHER INFORMATION: Artificial Sequence, Mimotope

<400> SEQUENCE: 116

Val Gln Pro Trp Asn Leu Glu Arg Leu Gln Pro Pro Arg
1               5                   10

<210> SEQ ID NO 117
<211> LENGTH: 13
<212> TYPE: PRT
<213> ORGANISM: Artificial Sequence
<220> FEATURE:
<223> OTHER INFORMATION: Artificial Sequence, Mimotope

<400> SEQUENCE: 117

Val Gln Pro Trp Ser Leu Glu Arg Leu Leu Pro Pro Arg
1               5                   10

<210> SEQ ID NO 118
<211> LENGTH: 13
<212> TYPE: PRT
<213> ORGANISM: Artificial Sequence
<220> FEATURE:
<223> OTHER INFORMATION: Artificial Sequence, Mimotope

<400> SEQUENCE: 118

Ser Val Pro Trp Ser Leu Glu Arg Leu Thr Pro Pro Arg
1               5                   10
```